(12) United States Patent
Odolczyk et al.

(10) Patent No.: US 10,463,639 B2
(45) Date of Patent: Nov. 5, 2019

(54) COMPOUNDS AS MODULATORS OF A MUTANT CFTR PROTEIN AND THEIR USE FOR TREATING DISEASES ASSOCIATED WITH CFTR PROTEIN MALFUNCTION

(71) Applicant: INSTYTUT BIOCHEMII I BIOFIZYKI PAN, Warsaw (PL)

(72) Inventors: Norbert Odolczyk, Warsaw (PL); Piotr Zielenkiewicz, Warsaw (PL); Grzegorz Wieczorek, Warsaw (PL); Aleksander Edelman, Chatenay-Malabry (FR); Danielle Tondelier, Le Mesnil-le-Roi (FR); Janine Fritsch, Saint Michel sur Orge (FR)

(73) Assignee: INSTYTUT BIOCHEMII I BIOFIZYKI PAN, Warzawa (PL)

( * ) Notice: Subject to any disclaimer, the term of this patent is extended or adjusted under 35 U.S.C. 154(b) by 46 days.

(21) Appl. No.: 14/969,609

(22) Filed: Dec. 15, 2015

(65) Prior Publication Data

US 2016/0113896 A1     Apr. 28, 2016

Related U.S. Application Data

(63) Continuation of application No. 14/829,234, filed on Aug. 18, 2015, now abandoned, which is a continuation-in-part of application No. 13/822,584, filed as application No. PCT/PL2011/000060 on Jun. 20, 2011, now abandoned.

(30) Foreign Application Priority Data

Sep. 14, 2010   (PL) ...................................... P392 396
Sep. 14, 2010   (PL) ...................................... P392 397

(51) Int. Cl.
| | |
|---|---|
| C07D 473/30 | (2006.01) |
| A61K 31/194 | (2006.01) |
| C07C 233/65 | (2006.01) |
| C07D 219/10 | (2006.01) |
| C07F 9/30 | (2006.01) |
| C07C 235/84 | (2006.01) |
| C07D 401/12 | (2006.01) |
| C07D 473/22 | (2006.01) |
| A61K 31/496 | (2006.01) |
| A61K 31/663 | (2006.01) |
| A61K 31/52 | (2006.01) |

(52) U.S. Cl.
CPC .......... *A61K 31/194* (2013.01); *A61K 31/496* (2013.01); *A61K 31/52* (2013.01); *A61K 31/663* (2013.01); *C07C 233/65* (2013.01); *C07C 235/84* (2013.01); *C07D 219/10* (2013.01); *C07D 401/12* (2013.01); *C07D 473/22* (2013.01); *C07D 473/30* (2013.01); *C07F 9/304* (2013.01); *C07F 9/305* (2013.01); *C07C 2603/18* (2017.05)

(58) Field of Classification Search
CPC .................................................. C07D 473/30
See application file for complete search history.

(56) References Cited

U.S. PATENT DOCUMENTS

2016/0101107 A1\*   4/2016   Odolczyk ............. C07C 233/65
                                                                514/263.34

OTHER PUBLICATIONS

Department of Chemistry at Purdue University. "Geometric Isomers." © 2017. Available from: <http://www.chem.purdue.edu/gchelp/cchem/geomi.html >.\*
Hunt, Ian. Department of Chemistry. University of Calgary. "Chapter 7: Stereochemistry." © 2017. Available from: <http://www.chem.ucalgary.ca/courses/351/Carey5th/Ch07/ch7-4.html >.\*
Jiang, H., et al. "Stabilizers of the Max Homodimer Identified in Virtual Ligand Screening Inhibit Myc Function." Molecular Pharmacology. (2009), vol. 76, pp. 491-502.\*
Jiang, H., et al. "Stabilizers of the Max Homodimer Identified in Virtual Ligand Screening Inhibit Myc Function." Molecular Pharmacology. (2009), vol. 76, pp. 491-502. (Year: 2009).\*
Waybright, T.J., et al. "Overcoming Problems of Compound Storage in DMSO: Solvent and Process Alternatives." Society for Biomolecular Sciences. (2009), pp. 708-715. (Year: 2009).\*

\* cited by examiner

*Primary Examiner* — Noble E Jarrell
*Assistant Examiner* — John S Kenyon
(74) *Attorney, Agent, or Firm* — McBee Moore Woodward & Vanik IP, LLC

(57) ABSTRACT

An exemplary embodiment relates to novel protein modulators capable of altering function of the mutant CFTR protein and their use for treating diseases associated with CFTR protein malfunction. The invention provides compositions, pharmaceutical preparations and methods of correcting the cellular alteration of a mutant CFTR protein wherein the CFTR mutation is a mutation ΔF508-CFTR, or another mutation of class II.

14 Claims, 8 Drawing Sheets

COMPOUNDS AS MODULATORS OF A MUTANT CFTR PROTEIN AND THEIR USE FOR TREATING DISEASES ASSOCIATED WITH CFTR PROTEIN MALFUNCTION

TECHNICAL FIELD

The exemplary techniques disclosed herein relate to novel protein modulators capable of altering function of the mutant CFTR protein and their use for treating diseases associated with CFTR protein malfunction. Exemplary embodiments provide compositions, pharmaceutical preparations and methods of correcting the cellular alteration of a mutant CFTR protein wherein the CFTR mutation is a mutation ΔF508-CFTR, or another mutation of class II.

BACKGROUND

Cystic fibrosis (also known as CF or mucoviscidosis) is one of the most common, fatal genetic diseases in humans. CF is an inherited autosomal recessive genetic disease that affects around 1 child in 2,500 live births. CF is caused by mutations in the cftr gene that encodes the cystic fibrosis transmembrane conductance regulator (CFTR protein) with activity as an epithelial chloride ion channel. As a result of impaired function of this protein, severe symptoms associated with respiratory and digestive systems and male reproductive system appear. To date, more than 1600 mutations in CFTR gene have been identified and described.

The CFTR gene mutations were classified into five classes based on the molecular mechanisms leading to the CFTR protein malfunction. The class I mutations contribute to the formation of proteins with incomplete length and usually involve the complete loss of its activity (e.g. G542X). Mutation in the class II lead to abnormal maturation of proteins in the endoplasmic reticulum and Golgi apparatus. The effect of these mutations is premature degradation of the protein. Hence, CFTR does not reach the cell membrane where it should perform its function (eg, ΔF508, ΔI507, S549R). The gene product having mutations of class III is properly synthesized, transported and incorporated into the cell membrane, but has decreased activity caused by abnormal regulation of the protein.

These mutations are frequently situated within one of the nucleotide binding domain. (eg. G551D/S). Mutations of class IV cause anomalies in the structure of the transmembrane protein and thereby reduce the conduction of chloride channel (e.g. R117H, R334W). Mutations altering the stability of mRNA represent a class V of the mutations of the CFTR gene (3849+10kbC->T,5T).

The most prevalent mutation present in at least one allele in approximately 90% of patients is a deletion of phenylalanine at position 508 of the CFTR amino acid sequence (ΔF508 CFTR). This is a classic example of class II mutation that causes premature degradation of the protein. This mutation is associated with water-electrolyte disturbances (among others with chloride anion flux out of a cell across the plasma membrane and the movement of sodium ions into the cell) and results in the appearance of pathological symptoms. Some of the most severe symptoms include congestion and increased mucus viscosity in the upper and lower airways leading to lung damage. These conditions create a favorable environment for development of bacterial infections caused by e.g. *Pseudomonas aeruginosa*. Moreover, malfunction of CFTR protein leads to obstruction of exocrine pancreatic ducts and related digestive disorders.

CFTR is a glycoprotein with 1480 amino acids and classified as an ABC (ATP-binding cassette) transporter. The protein consists of five domains. There are two nucleotide binding domains (NBD1 and NBD2), regulatory domain (RD) and two transmembrane domains (TMD1 and TMD2). The protein activity is regulated by cAMP-dependent Protein Kinase (PKA) which catalyze phosphorylation of regulatory domain (RD) and also by binding of two ATP molecules to NBD1 and NBD2 domains.

The disclosure in the patent application WO2007075901 (publ. Jul. 5, 2007) relates to prodrugs of modulators of ABC transporters, particularly, CFTR modulators, compositions thereof, and methods therewith. An exemplary embodiment also relates to methods of treating ABC transporter mediated diseases using such modulators.

In U.S. Patent Publication No. 20080319008, compounds that increase activity (ion transport) of a mutant CFTR protein, and uses thereof are described. The disclosure also provides compositions, pharmaceutical preparations and methods increasing ion transport activity of a mutant CFTR protein, i.e. ΔF508 CFTR, G551D-CFTR, G1349D-CFTR or D1152H-CFTR, that are suitable in treating cystic fibrosis (CF). The compositions and pharmaceutical preparations of the disclosure may comprise one or more phenylglycine-containing compounds or sulfonamide-containing compounds or an analog or derivatives thereof.

In a publication WO2009051910, compounds that increase ion transport activity of a mutant CFTR protein, and uses thereof are described. The disclosure provides compositions, pharmaceutical preparations and methods for increasing activity of a mutant-CFTR. The compositions, pharmaceutical preparations and methods are notable for the study and treatment of disorders associated with mutant-CFTR, such as cystic fibrosis. The compositions and pharmaceutical preparations of the disclosure may comprise one or more phenylglycine-containing compounds, or an analog or derivative thereof.

U.S. Pat. No. 5,948,814 describes the use of genistein compound for treatment of CF. A method of treating cystic fibrosis by generating CFTR function in cells containing mutant CFTR and the therapeutic composition for treatment are described. The method of treatment comprises administering an effective amount of genistein, or genistein analogues and derivatives, to a patient afflicted with cystic fibrosis.

In U.S. Patent Publication No. 20040006127, a method for activation of the chloride is described. Fluorescein and derivatives have use in the treatment of a disease condition of a living animal body, including human, which disease is responsive to the activation of the CFTR chloride channels, for instance cystic fibrosis, disseminated brocheiectasis, pulmonary infections, chronic pancreatitis, male infertility and long QT syndrome.

In U.S. Patent Application No. 20080318984, compounds for correction of the cellular alteration of a mutant CFTR protein and uses thereof are described. The disclosure provides for compositions, pharmaceutical preparations and methods for correcting cellular processing of a mutant-CFTR protein (e.g., ΔF508 CFTR) that are notable for the treatment of cystic fibrosis. The compositions and pharmaceutical preparations of the disclosure may comprise one or more aminobenzothiazole-containing compounds, aminoarylthiazole-containing compounds, quinazolinylaminopyrimidinone-containing compounds, bisaminomethylbithiazole-containing compounds, or phenylaminoquinoline-containing compounds, or an analog or derivative thereof.

In a publication WO2009051909, compounds that improve the cellular alteration of a mutant CFTR protein and uses thereof are described. The disclosure provides compositions, pharmaceutical preparations and methods for increasing activity of a mutant-CFTR. The compositions, pharmaceutical preparations and methods are notable for the study and treatment of disorders associated with mutant-CFTR, such as cystic fibrosis. The compositions of the disclosure may comprise one or more bithiazole-containing compounds, or an analog or derivative thereof.

Phenylalanine 508 in CFTR protein occurs on the surface of NBD1 domain of CFTR. Current structural and biophysical studies reveal no significant differences between wild-domain protein, and ΔF508 mutant domain that may affect the folding kinetics and thermodynamic stability of CFTR protein. Solved crystal structures of both domains show only slight differences in the reorganization of the amino acids located near the site, which should be occupied by F508.

Each of the forgoing patents and publications are incorporated herein by reference in their entirety.

SUMMARY

The object of exemplary embodiments is to provide compositions, pharmaceutical preparations and methods of correcting the cellular processing of mutant CFTR protein. F508 deletion has minimal effect on the structure of NBD1 domain as observed in the results of X-rays, and cannot explain the dramatic difference in the behavior of mutant and native forms of CFTR protein in the cell. For the purposes of an exemplary embodiment, the structural data of both forms of protein were subjected to computer simulation designed to determine the dynamic properties of NBD1. In an exemplary embodiment the molecular dynamics methods have been used. This method is based on an iterative calculation of the interactions between the atoms forming the simulated system and solving equations of motion. These simulations (for both studied forms of NBD1) results in sets of structures that can be adopted by the target protein according to the initial physical assumptions—the so-called trajectories.

Based on the analysis of molecular dynamics trajectories of the two domains it is possible to isolate a mutant protein conformation, which differs significantly from the conformational states adopted by the wild protein. The conformation possesses the two major pockets on the surface of the protein located on both sides of the ATP binding site. The structure of protein in this conformation was used to develop compounds for the correction of ΔF508-CFTR activity.

DETAILED DESCRIPTION

Figure 1:
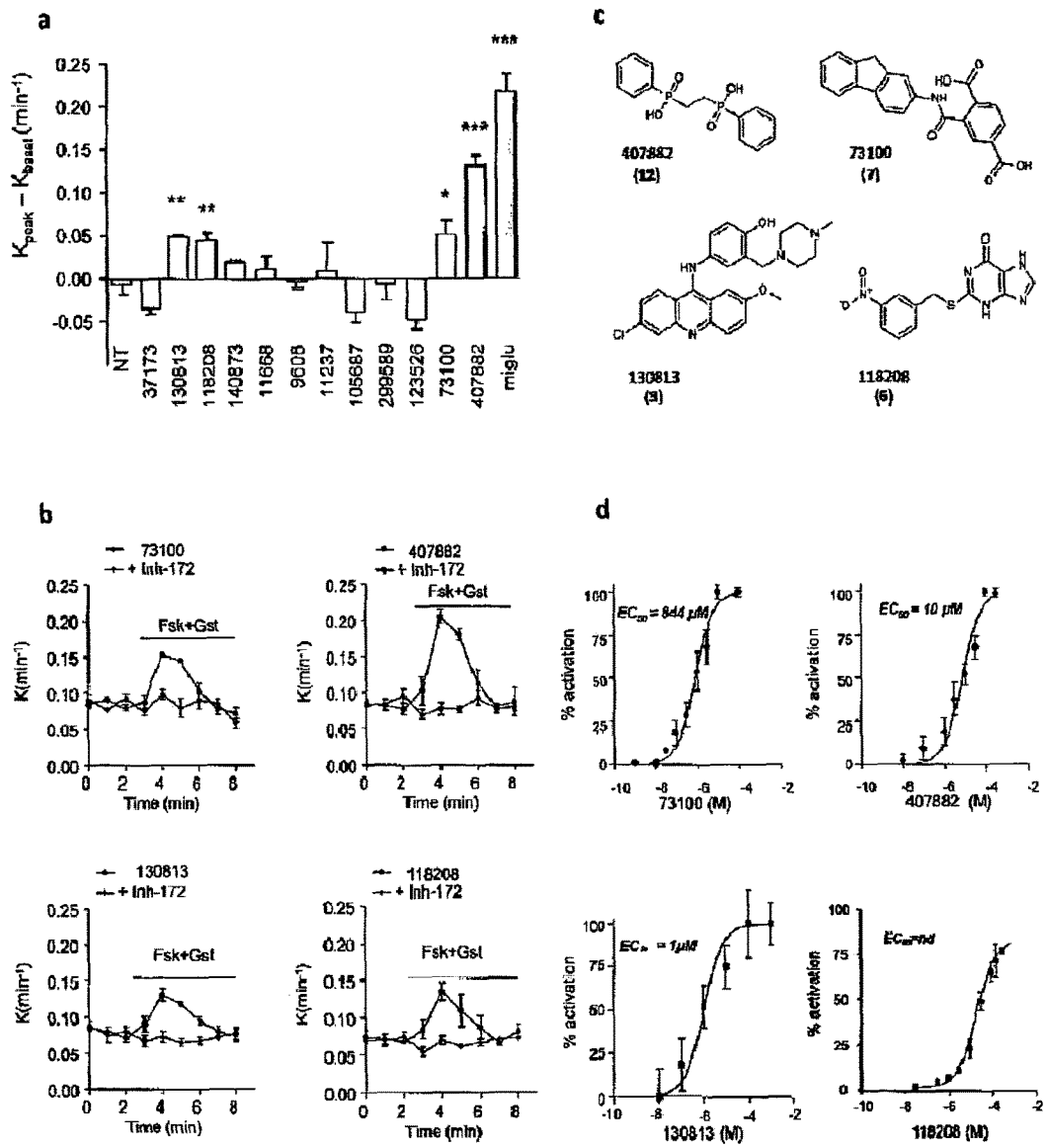
FIG. 1 indicated effects of different compounds on iodide efflux at 1 μM in ΔF508-CFTR HeLa cells.

Exemplary embodiments will be described. Various modifications, adaptations or variations of the exemplary embodiments described herein may become apparent to those skilled in the art as such are disclosed. It will be understood that all such modifications, adaptations or variations that rely upon the teachings hereof, and through which these teachings have advanced the art, are considered to be within the scope and spirit of the disclosure presented herein.

The methods and compositions of the exemplary embodiments may suitably comprise, consist of, or consist essentially of the components, ingredients, elements, steps and process delineations described herein. The embodiments illustratively disclosed herein suitably may be practiced in the absence of any element, process step, or ingredient which is not specifically disclosed herein.

Unless otherwise stated, all percentages, parts, and ratios expressed herein are based upon weight of the total compositions.

The headings provided herein serve to illustrate, but not to limit the teachings herein in any way or manner.

An exemplary embodiment is a compound of general formula (I):

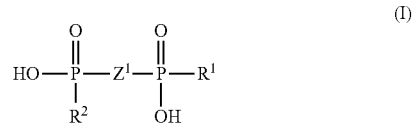

(I)

its tautomers, E and Z geometrical isomers, optically active forms such as enantiomers, diastereomers and their racemate forms or a mixture of stereoisomeric forms or its pharmaceutically acceptable salts thereof or complexes thereof;

wherein $Z^1$ is independently selected from the group consisting of:

—$C_nH_{(2n)}$—, which is branched or unbranched wherein n is an integer from 1 to 5; —$C_nH_{(2n-2)}$— in E or Z geometrical conformation which is branched or unbranched wherein n is an integer from 2 to 5; —$C_nH_{(2n-4)}$— which is branched or unbranched wherein n is an integer from 2 to 5; —CR'H, —$C_2H_3R'$, E or Z—$C_2HR'$—, —$C_3H_5R'$—, E or Z—$C_3H_3R'$—, —$OCH_2$—, —$CH_2O$—, —NR"$CH_2$—, —$CH_2$NR"—; wherein R' is independently selected from the group consisting of: —H, halogen, —$NH_2$, —OH, —CN, $CF_3$, —$CHF_2$, —$CH_2F$, —SH, —SCN, —$CH_3$, —$C_2H_5$; wherein R" is independently selected from the group consisting of: —H, —$CH_3$, —$C_2H_5$; wherein $R^1$ and $R^2$ are independently selected from the group consisting of aromatic ring or heteroaromatic ring, as a modulator of a mutant CFTR protein for use in the treatment of cystic fibrosis. $R^1$ and $R^2$ are independently selected from the group of sub-formula (Ia):

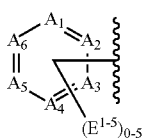

(Ia)

wherein $A_1, A_2, A_3, A_4, A_5, A_6$ is independently selected N or C atoms wherein ring contain 0-3 nitrogen atoms; wherein $E^1$, $E^2$, $E^3$, $E^4$, $E^5$ represents optional substituents, which are selected from: —$OR_B$, —$OC(=O)R_C$, —$OC(=O)OR_B$, —$OC(=O)N(R_A)R_A'$, —$C(=O)R_C$, —$C(=O)N(R_A)R_A'$, —$C(=O)N(OR_B)R_A$, —$C(=O)OR_B$, —$C(=S)R_C$, —$C(=O)C(=O)R_C$, —$CH_2OR_B$, —$CH_2CH_2OR_B$, —$CH_2N(R_A)R_A'$, —$CH_2CH_2N(R_A)R_A'$, —$CH_2OCH_2R_C$, —$CH_2N(R_A)CH_2R_C$, —$SR_D$, —$S(=O)R_D$, —$SO_2R_D$, —$SO_2N(R_A)R_A'$, —$SO_3R_B$, —$N(R_A)C(=O)R_C$, —$N(R_A)C(=O)OR_B$, —$N(R_A)C(=O)N(R_A')R_A''$, —$N(R_A)SO_2R_D$, —$N(R_A)SO_2NR_A'R_A''$, —$N(R_A)R_A'$, —$N(R_A)C(=O)R_C$, —$N(R_A)C(=O)OR_B$, —$N(R_A)N(R_A')R_A''$, —$N(R_A')N(R_A)C(=O)R_C$, —$NO_2$, —$CN$, —$CF_3$, —$CHF_2$, —$CH_2F$, —$NH_2$, —$SCN$, —$SO_2CN$, —F, —Cl, —Br, —I, —$PO_3H_2$, —$OPO_3H_2$, —$C_nH_{2n}R_C$ which is branched or unbranched wherein n is an integer from 1 to 5; —$C_nH_{(2n-2)}R_C$ in E or Z geometrical conformation which branched or unbranched wherein n is an integer from 2 to 5; —$C_nH_{(2n-4)}R_C$ which is branched or unbranched wherein n is an integer from 2 to 5;

wherein $R_A$, $R_A'$, $R_A''$ are each independently selected from the group consisting of: —H, lower alkyl group, —CN, —$CF_3$, —$CHF_2$, —$CH_2F$, —OH;

wherein $R_B$ is independently selected from the group consisting of: —H, lower alkyl group, —CN, —$CF_3$, —$CHF_2$, —$CH_2F$, —$CH_2Cl$, —$CH_2Br$, —$CH_2I$;

wherein $R_C$ is independently selected from the group consisting of: —H, lower alkyl group, —CN, —$CF_3$, —$CHF_2$, —$CH_2F$, —$CH_2Cl$, —$CH_2Br$, —$CH_2I$, —F, —Cl, —Br, —I, —$NH_2$, wherein $R_D$ is independently selected from the group consisting of: —H, lower alkyl group;

An exemplary embodiment of the compound is represented by the following structures:

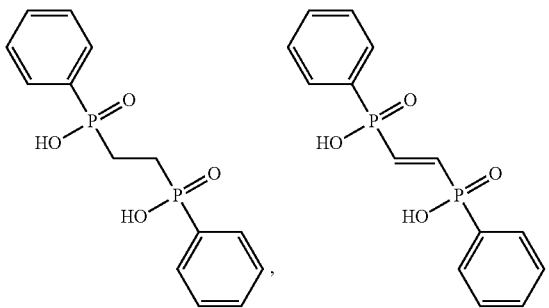 [SMILES: O=P(O)(CCP(=O)(O)c1ccccc1)c1ccccc1 ; O=P(O)(/C=C/P(=O)(O)c1ccccc1)c1ccccc1]

An exemplary embodiment of the compound has effect on mutant CFTR protein, wherein said CFTR mutation is a mutation ΔF508-CFTR, or another mutation of class II and where a mutation ΔF508-CFTR, or another mutation of class II are involved in CFTR protein malfunction.

In an exemplary embodiment the CFTR protein malfunction occurs in the protein associated with the disease cystic fibrosis.

A further exemplary embodiment is a modulator according to the above, for use in the treatment of cystic fibrosis wherein it has effect on CFTR-dependent ion transport across cellular membrane and/or it has the ability to increase the number of mutant CFTR proteins that reach the cell surface.

An exemplary embodiment is used in the treatment of cystic fibrosis wherein it has stabilizing effect on the structure of the mutant CFTR protein and/or blocks the interaction with cellular proteins responsible for the premature degradation of mutant CFTR An exemplary embodiment is used in the treatment of cystic fibrosis wherein it has effect on mutant CFTR protein, wherein said CFTR mutation is a mutation ΔF508-CFTR, or another mutation of class II.

An exemplary embodiment are compounds, modulators of a mutant CFTR protein, of general formula (II):

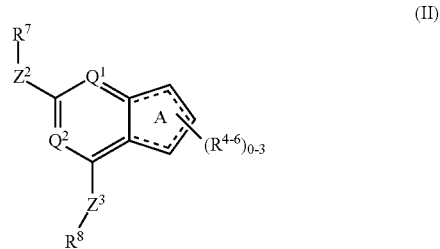

(II)

its tautomers, E and Z geometrical isomers, optically active forms such as enantiomers, diastereomers and their racemate forms or a mixture of stereoisomeric forms or its pharmaceutically acceptable salts thereof or complexes thereof;

wherein $Q^1$ and $Q^2$ are independently selected from the group consisting of: C, CH, N, NH;

wherein A is a fused five-membered ring having 0-3 independently selected heteroatoms wherein the heteroatoms comprise nitrogen, sulfur or oxygen;

wherein $R^4$, $R^5$ and $R^6$ represent optional substituents, which are independently selected from: —$OR_B$, —$OC(=O)R_C$, —$OC(=O)OR_B$, —$OC(=O)N(R_A)R_A'$, —$C(=O)R_C$, —$C(=O)N(R_A)R_A'$, —$C(=O)N(OR_B)R_A$, —$C(=O)OR_B$, —$C(=S)R_C$, —$C(=O)C(=O)R_C$, —$CH_2OR_B$, —$CH_2CH_2OR_B$, —$CH_2N(R_A)R_A'$, —$CH_2CH_2N(R_A)R_A'$, —$CH_2OCH_2R_C$, —$CH_2N(R_A)CH_2R_C$, —$SR_D$, —$S(=O)R_D$, —$SO_2R_D$, —$SO_2N(R_A)R_A'$, —$SO_3R_B$, —$N(R_A)C(=O)R_C$, —$N(R_A)C(=O)OR_B$, —$N(R_A)C(=O)N(R_A')R_A''$, —$N(R_A)SO_2R_D$, —$N(R_A)SO_2N(R_A')R_A''$, —$N(R_A)R_A'$, —$N(R_A)C(=O)R_C$, —$N(R_A)C(=O)OR_B$, —$N(R_A)N(R_A')R_A''$, —$N(R_A')N(R_A)C(=O)R_C$, —CN, —$CF_3$, —$CHF_2$, —$CH_2F$, —$NH_2$, —SCN, —$SO_2CN$, —F, —Cl, —Br, —I, —$PO_3H_2$, —$OPO_3H_2$, which may be optionally preceded by: —$C_nH_{(2n-1)}R_C$ which is branched or unbranched wherein n is an integer from 1 to 4; —$C_nH_{(2n-3)}R_C$ in E or Z geometrical conformation which is branched or unbranched wherein n is an integer from 2 to 5; —$C_nH_{(2n-5)}R_C$ which is branched or unbranched wherein n is an integer from 2 to 5;

wherein $Z^2$ is selected from: a single bond, —$N(R_A')$—, —S—, —S-alkil-, —O—, —O-alikil-, —$C(=O)$—, —$S(=O)$—, —$OC(=O)$—, —$C(=O)N(R_A')$—, —$OC(=O)N(R_A')$—, —$C(=O)O$—, —$SO_2$—, —$SO_2N(R_A')$—, —$N(R_A')SO_2$—, —$N(R_A')SO_2N(R_A'')$—, —$CH_2O$—, —$N(R_A')C(=O)$—, —$N(R_A')C(=O)O$—, —$N(R_A')C(=O)N(R_A'')$—, —$C(=O)C(=O)$—, —$N(R_A')C(=O)O$—, —$N(R_A')N(R_A'')$—, —$N(R_A')N$ ($R_A''$)C(=O)—, —C(=O)N($R_A'$)N($R_A''$)—, —CH$_2$N ($R_A'$)—, —CH$_2$CH$_2$O—, —CH$_2$CH$_2$N($R_A'$)—, —CH$_2$OCH$_2$—, —CH$_2$N($R_A'$)CH$_2$—, —C$_n$H$_{2n}$— which is branched or unbranched wherein n is an integer from 1 to 5;

—C$_n$H$_{(2n-2)}$— in E or Z geometrical conformation which is branched or unbranched wherein n is an integer from 2 to 5; —C$_n$H$_{(2n-4)}$ which is branched or unbranched wherein n is an integer from 2 to 5;

wherein R$^7$ are independently selected from the group consisting of: —H, aromatic ring or heteroaromatic ring;

wherein Z$^3$ is selected from: a single bond, double bond, —N($R_A'$)—, —S—, —S-alkyl-, —O—, —O-alkyl-C(=O)—, —C(=S)—, —OC(=O)—, —C(=O)N($R_A'$)—, —OC(=O)N($R_A'$)—, —C(=O)O—, —SO$_2$—, —SO$_2$N($R_A'$)—, —N($R_A'$)SO$_2$—, —N($R_A'$)SO$_2$N($R_A'$)—, —CH$_2$O—, —N($R_A'$)C(=O)—, —N($R_A'$)C(=O)O—, —N($R_A'$)C(=O)N($R_A''$)—, —C(=O)C(=O)—, —N($R_A'$)C(=O)O—, —N($R_A'$)N($R_A''$)—, —N($R_A'$)N ($R_A''$)C(=O)—, —C(=O)N($R_A'$)N($R_A''$)—, —CH$_2$N ($R_A'$)—, —CH$_2$CH$_2$O—, —CH$_2$CH$_2$N($R_A'$)—, —CH$_2$OCH$_2$—, —CH$_2$N($R_A'$)CH$_2$—, —C$_n$H$_{2n}$— which is branched or unbranched wherein n is an integer from 1 to 5;

—C$_n$H$_{(2n-2)}$— in E or Z geometrical conformation which is branched or unbranched wherein n is an integer from 2 to 5; —C$_n$H$_{(2n-4)}$ which is branched or unbranched wherein n is an integer from 2 to 5;

wherein R$^8$ is selected from: H, O, S, aromatic ring or heteroaromatic ring; —C$_n$H$_{(2n+1)}$ which is branched or unbranched wherein n is an integer from 1 to 5; —C$_n$H$_{(2n-1)}$ in E or Z geometrical conformation which is branched or unbranched wherein n is an integer from 2 to 5; —C$_n$H$_{(2n-3)}$ which is branched or unbranched wherein n is an integer from 2 to 5;

wherein $R_A$, $R_A'$, $R_A''$ are each independently selected from the group consisting of: —H, lower alkyl group, —CN, —CF$_3$, —CHF$_2$, —CH$_2$F, —OH;

wherein $R_B$ is independently selected from the group consisting of: —H, lower alkyl group, —CN, —CF$_3$, —CHF$_2$, —CH$_2$F, —CH$_2$Cl, —CH$_2$Br, —CH$_2$I;

wherein $R_C$ is independently selected from the group consisting of: —H, lower alkyl group, —CN, —CF$_3$, —CHF$_2$, —CH$_2$F, —CH$_2$Cl, —CH$_2$Br, —CH$_2$I, —F, —Cl, —Br, —I, —NH$_2$;

wherein $R_D$ is independently selected from the group consisting of: —H, lower alkyl group;

wherein the 5-membered ring A is moiety selected from the group consisting of:

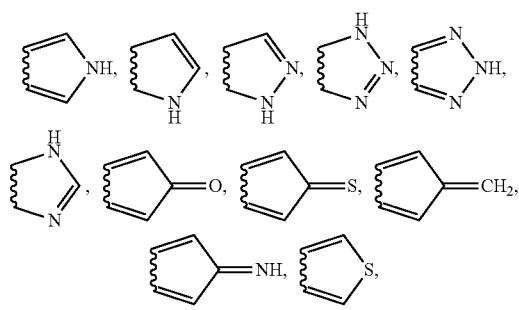

and wherein compound 6-[(4-oxo-1H-quinolin-3-yl)carbonylamino]-1H-indole-4-carboxylic acid ethyl ester is excluded, as a modulator of a mutant CFTR protein, for use in the manufacture of a medicament for the treatment of diseases associated with CFTR protein malfunction.

An exemplary embodiment of the compound described above has the general formula (IIa) or (IIb):

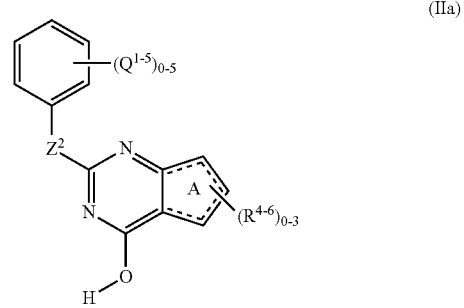

(IIa)

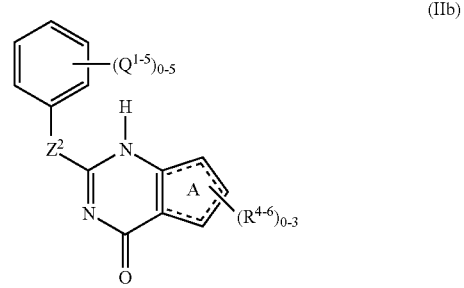

(IIb)

wherein Q$^1$, Q$^2$, Q$^3$, Q$^4$, Q$^5$ represent optional substituents which are independently selected from the group consisting of: —OR$_B$, —OC(=O)R$_C$, —OC(=O)OR$_B$, —OC(=O)N ($R_A$)$R_A'$, —C(=O)R$_C$, —C(=O)N($R_A$)$R_A'$, —C(=O)N (OR$_B$)$R_A$, —C(=O)OR$_B$, —C(=S)R$_C$, —C(=O)C(=O)R$_C$, —CH$_2$OR$_B$, —CH$_2$CH$_2$OR$_B$, —CH$_2$N($R_A$)$R_A'$, —CH$_2$CH$_2$N($R_A$)$R_A'$, —CH$_2$OCH$_2$R$_C$, —CH$_2$N($R_A$) CH$_2$R$_C$, —SR$_D$, —S(=O)R$_D$, —SO$_2$R$_D$, —SO$_2$N($R_A$)$R_A'$, —SO$_3$R$_B$, —N($R_A$)C(=O)R$_C$, —N($R_A$)C(=O)OR$_B$, —N($R_A$)C(=O)N($R_A'$)$R_A''$, —N($R_A$)SO$_2$R$_D$, —N($R_A$) SO$_2$N($R_A'$)$R_A''$, —N($R_A$)$R_A'$, —N($R_A$)C(=O)R$_C$, —N($R_A$) C(=O)OR$_B$, —N($R_A$)N($R_A'$)$R_A''$, —N($R_A'$)N($R_A$)C(=O) R$_C$, —NO$_2$, —CN, —CF$_3$, —CHF$_2$, —CH$_2$F, —NH$_2$, —SCN, —SO$_2$CN, —F, —Cl, —Br, —I, —C$_n$H$_{2n}$R$_C$ which is branched or unbranched wherein n is an integer from 1 to 5; —C$_n$H$_{(2n-2)}$Rc in E or Z geometrical conformation which is branched or unbranched wherein n is an integer from 2 to 5; —C$_n$H$_{(2n-4)}$Rc which is branched or unbranched wherein n is an integer from 2 to 5; —PO$_3$H$_2$, —OPO$_3$H$_2$.

An exemplary embodiment of the compound may be represented by the following structure:

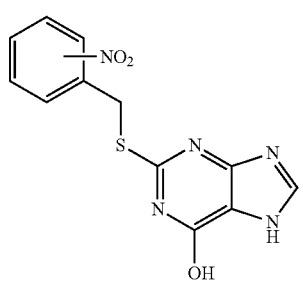

An exemplary embodiment of the compound has effect on mutant CFTR protein, wherein said CFTR mutation is a mutation ΔF508-CFTR, or another mutation of class II and where a mutation ΔF508-CFTR, or another mutation of class II are involved in CFTR protein malfunction.

In an exemplary embodiment the CFTR protein malfunction occurs in the protein associated with the disease cystic fibrosis.

A further exemplary embodiment is a modulator according to the above, for use in the treatment of cystic fibrosis wherein it has effect on CFTR-dependent ion transport across cellular membrane and/or it has the ability to increase the number of mutant CFTR proteins that reach the cell surface.

An exemplary embodiment is used in the treatment of cystic fibrosis wherein it has stabilizing effect on the structure of the mutant CFTR protein and/or blocks the interaction with cellular proteins responsible for the premature degradation of mutant CFTR An exemplary embodiment is used in the treatment of cystic fibrosis wherein it has effect on mutant CFTR protein, wherein said CFTR mutation is a mutation ΔF508-CFTR, or another mutation of class II.

An exemplary embodiment is a compound of general formula (III):

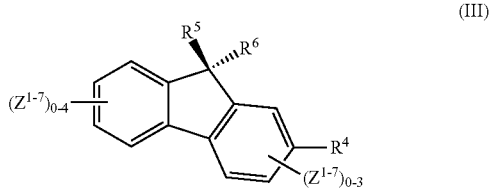

(III)

its tautomers, E and Z geometrical isomers, optically active forms such as enantiomers, diastereomers and their racemate forms or a mixture of stereoisomeric forms or its pharmaceutically acceptable salts thereof or complexes thereof;

wherein $Z^1$, $Z^2$, $Z^3$, $Z^4$, $Z^5$, $Z^6$, $Z^7$ represents optional substituents, which are selected from substituents consisting at least one atom selected from the group consisting of: C, N, S, O, H, P, F, Cl, Br, I;

wherein $R^4$ represents optionally substituted moiety of formula (IIIa):

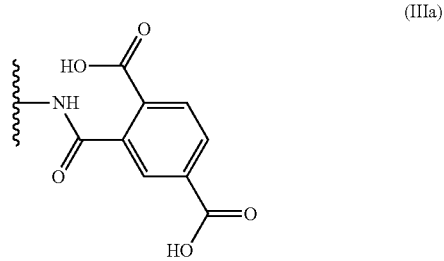

(IIIa)

wherein $R^5$ and $R^6$ are optional substituents which are independently selected from the group consisting of: OH, $NH_2$, COOH, Cl, Br, I, $CH_3$, $C_2H_5$;

and having a general formula (IIIb):

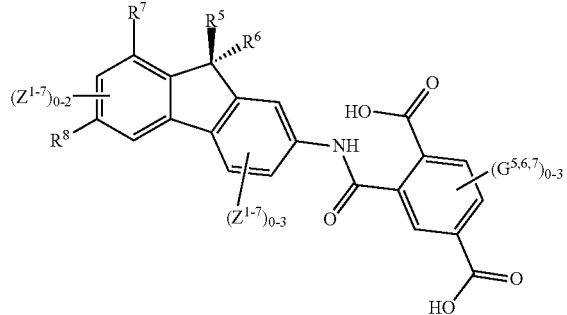

(IIIb)

wherein $R^7$ is an optional substituent which is independently selected from the group consisting of: —F, —Cl, —Br, —I, —$CH_3$, —$C_2H_5$;

wherein $R^8$ is an optional substituent which is independently selected from the group consisting of: —$NH_2$, —NHAr, —OH, —$CH_2Ar$, —C(=O)Ar, —OAr;

wherein Ar is an aromatic group or heteroaromatic group;

wherein $Z^1$, $Z^2$, $Z^3$, $Z^4$, $Z^5$, $Z^6$, $Z^7$ represent optional substituents which are independently selected from the group consisting of: —$OR_B$, —OC(=O)$R_C$, —OC(=O)$OR_B$, —OC(=O)N($R_A$)$R_A$', —C(=O)$R_C$, —C(=O)N($R_A$)$R_A$', —C(=O)N($OR_B$)$R_A$, —C(=O)$OR_B$, —C(=S)$R_C$, —C(=O)C(=O)$R_C$, —$CH_2OR_B$, —$CH_2CH_2OR_B$, —$CH_2$N($R_A$)$R_A$', —$CH_2CH_2$N($R_A$)$R_A$', —$CH_2OCH_2R_C$, —$CH_2$N($R_A$)$CH_2R_C$, —$SR_D$, —S(=O)$R_D$, —$SO_2R_D$, —$SO_2$N($R_A$)$R_A$', —$SO_3R_B$, —N($R_A$)C(=O)$R_C$, —N($R_A$)C(=O)$OR_B$, —N($R_A$)C(=O)N($R_A$')$R_A$'', —N($R_A$)$SO_2R_D$, —N($R_A$)$SO_2$N($R_A$')$R_A$'', —N($R_A$)$R_A$', —N($R_A$)C(=O)$R_C$, —N($R_A$)C(=O)$OR_B$, —N($R_A$)N($R_A$')$R_A$'', —N($R_A$')N($R_A$)C(=O)$R_C$, —$NO_2$, —CN, —$CF_3$, —$CHF_2$, —$CH_2F$, —$NH_2$, —SCN, —$SO_2$CN, —F, —Cl, —Br, —I, —$C_nH_{2n}R_C$ which is branched or unbranched wherein n is an integer from 1 to 5; —$C_nH_{(2n-2)}R_C$ in E or Z geometrical conformation which is branched or unbranched wherein n is an integer from 2 to 5; —$C_nH_{(2n-4)}R_C$ which is branched or unbranched wherein n is an integer from 2 to 5, —$PO_3H_2$, —$OPO_3H_2$;

wherein $R_A$, $R_A$', $R_A$'' are each independently selected from the group consisting of: —H, lower alkyl group, —CN, —$CF_3$, —$CHF_2$, —$CH_2F$, —OH;

wherein $R_B$ is independently selected from the group consisting of: —H, lower alkyl group, —CN, —$CF_3$, —$CHF_2$, —$CH_2F$, —$CH_2Cl$, —$CH_2Br$, —$CH_2I$;

wherein $R_C$ is independently selected from the group consisting of: —H, lower alkyl group, —CN, —$CF_3$, —$CHF_2$, —$CH_2F$, —$CH_2Cl$, —$CH_2Br$, —$CH_2I$, —F, —Cl, —Br, —I, —$NH_2$;

wherein $R_D$ is independently selected from the group consisting of: —H, lower alkyl group, as a modulator of a mutant CFTR protein, for use in the manufacture of a medicament for the treatment of diseases associated with CFTR protein malfunction.

An exemplary embodiment of the compound is represented by the following structure:

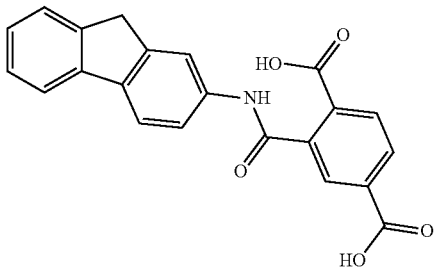 [SMILES: O=C(O)c1ccc(C(=O)O)c(C(=O)Nc2ccc3c(c2)Cc2ccccc2-3)c1]

An exemplary embodiment of the compound has effect on mutant CFTR protein, wherein said CFTR mutation is a mutation ΔF508-CFTR, or another mutation of class II and where a mutation ΔF508-CFTR, or another mutation of class II are involved in CFTR protein malfunction.

In an exemplary embodiment the CFTR protein malfunction occurs in the protein associated with the disease cystic fibrosis.

A further exemplary embodiment is a modulator according to the above, for use in the treatment of cystic fibrosis wherein it has effect on CFTR-dependent ion transport across cellular membrane and/or it has the ability to increase the number of mutant CFTR proteins that reach the cell surface.

An exemplary embodiment is used in the treatment of cystic fibrosis wherein it has stabilizing effect on the structure of the mutant CFTR protein and/or blocks the interaction with cellular proteins responsible for the premature degradation of mutant CFTR An exemplary embodiment is used in the treatment of cystic fibrosis wherein it has effect on mutant CFTR protein, wherein said CFTR mutation is a mutation ΔF508-CFTR, or another mutation of class II.

An exemplary embodiment is a compound of general formula (IV):

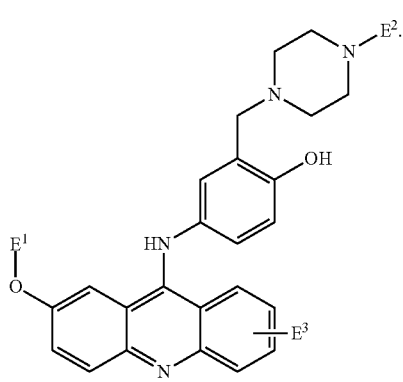

its esters, ethers, tautomers, E and Z geometrical isomers, optically active forms such as enantiomers, diastereomers and their racemate forms or a mixture of stereoisomeric forms or its pharmaceutically acceptable salts thereof or complexes thereof;

wherein $E^1$, $E^2$ represent substituents which are independently selected from: H, —CH$_3$, —C$_2$¾; wherein E represents optional substituent selected from: —Cl, —F, —Br, —I, —CF$_3$, —CHF$_2$, —CH$_2$F, —CH$_2$Cl, —CH$_2$Br, —CH$_2$I, optionally substituted lower alkyl group;

An exemplary embodiment of the compound is represented by the following structure:

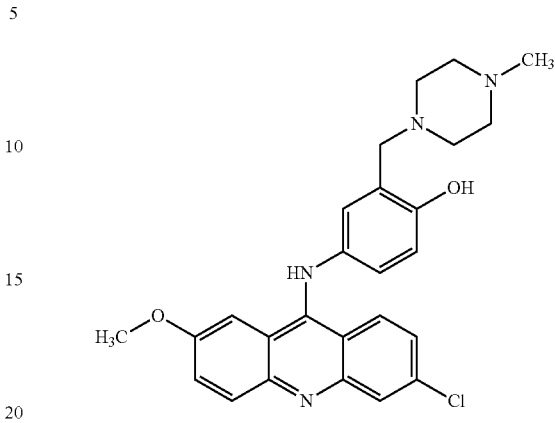

An exemplary embodiment of the compound has effect on mutant CFTR protein, wherein said CFTR mutation is a mutation ΔF508-CFTR, or another mutation of class II and where a mutation ΔF508-CFTR, or another mutation of class II are involved in CFTR protein malfunction.

In an exemplary embodiment the CFTR protein malfunction occurs in the protein associated with the disease cystic fibrosis.

A further exemplary embodiment is a modulator according to the above, for use in the treatment of cystic fibrosis wherein it has effect on CFTR-dependent ion transport across cellular membrane and/or it has the ability to increase the number of mutant CFTR proteins that reach the cell surface.

An exemplary embodiment is used in the treatment of cystic fibrosis wherein it has stabilizing effect on the structure of the mutant CFTR protein and/or blocks the interaction with cellular proteins responsible for the premature degradation of mutant CFTR An exemplary embodiment is used in the treatment of cystic fibrosis wherein it has effect on mutant CFTR protein, wherein said CFTR mutation is a mutation ΔF508-CFTR, or another mutation of class II.

FIG. 1

The effects of different compounds on iodide efflux at 1 μM in ΔF508-CFTR HeLa cells.

(a) bar graph showing the peak amplitudes of Fsk/Gsk dependent iodide effluxes in cells treated by the different drugs as in A. Values are mean of 3 independent experiments. *p<0.05, **p<0.01.

(b) chemical structures of active correctors identified in silico (c) examples of iodide efflux curves obtained in HeLa cells stably transfected with ΔF508-CFTR and treated for 24 hours with 10 μM with different compounds. CFTR dependent response was induced by 10 μM Forskolin (Fsk)+30 μM Genistein (Gsk) as indicated by the horizontal bar above the traces.

(d) EC50 was determined for active compounds of pocket 2: 407882 and 73100 and one of pocket 1: 130813, for 118208 EC50 could not be precisely determined since the maximum of iodide efflux was not reached even at 100 μM (also shown).

FIG. 2

To test whether the compounds exhibit potentiator activity independent of their effect on CFTR trafficking, we examined iodide efflux in untreated WT-CFTR HeLa cells. Compounds were added along with forskolin and their effects were compared to that of forskolin alone or forskolin plus genistein. Unlike genistein, all tested molecules induced an I$^-$ efflux greater than that of forskolin alone.

FIG. 3

Potentiation was also tested in ΔF508-CFTR HeLa cells treated for 2 hours with miglustat to rescue ΔF508-CFTR. I$^-$ efflux was stimulated either with forskolin alone, with forskolin plus genistein or forskolin plus the different compounds. As shown in the Figure, only genistein was able to increase efflux, demonstrating the absence of potentiation activity by The drugs.

FIG. 4

Impact of identified correctors on ΔF508-CFTR maturation and cell localization.

(a) Effects of different compounds on CFTR processing. Representative immunoblots of WT-CFTR and ΔF508-CFTR proteins of the proteins from HeLa cells treated with 1 μM of the different compounds for 24 hours with Mab 24-1. The positions of the mature (band C) and immature (band B) forms of CFTR are indicated.

(b) Comparison of relative intensity (C/B+C) for WT-CFTR, ΔF508-CFTR alone and ΔF508-CFTR after correction with our molecules.

(c) Effects of the different compounds used at 1 μM on CFTR localization. Confocal imaging showing the plasma membrane localisation of WT-CFTR and intracellular localisation of ΔF508-CFTR. The effect of drugs is illustrated in panels c to f. Bars: 20 μM. Arrows indicate staining of CFTR at the plasma membrane.

FIG. 5

Synergistic effect of active compounds on iodide efflux tested at 1 μM.

(a) Iodide efflux in response to 1 μM Forskolin (Fsk)+30 μM Genistein (Gsk) as indicated by the horizontal bar above the traces, for cells treated for 24 h with a tested compounds alone and in combination as fallows (a) 407882, 118208, (b) 118208, 73100 (c) 407882, 37173. (d) bar graph showing the peak amplitudes of Fsk/Gst dependent iodide effluxes in cells treated by the different drugs as in. Values are mean of 3 independent experiments. *$p<0.05$, **$p<0.01$

FIG. 6

(a)/(b) Current-voltage relationship for cAMP-dependent chloride currents in HeLa cells treated with 407882(12) plus 118208(6) compounds at 1 μM.

FIG. 7

The effects of different compounds on iodide efflux at 1 μM in an epithelial serous cell line derived from a ΔF508 CF patient (CF-4KM) cells. The concentration-dependence has been shown for the most potent molecule 407882

FIG. 8

The effect of 73100 plus 118208 molecules on nasal potential difference ($\Delta V_{TE}$) in ΔF508/ΔF508 mice. Basal $V_{TE}$ values and $\Delta V_{TE}$ changes induced by perfusion of nasal epithelium with 100 μM amiloride, $\Delta V_{TEamil}$ were similar in mice treated with the two molecules or with liposomes alone. Perfusion of low Cl$^-$ solution in 3 out of 5 mice hyperpolarized $V_{TE}$ by more than 2 mV ($\Delta V_{TEamil-lowCl}$) i.e. the threshold value established by us as significant effect of treatment. The CFTR-related current unmasked by CFTR inhibitor $I_{Inh172}$ represents about 30% of ($\Delta V_{TEamil-lowCl}$) (data not shown).

For a better understanding of some exemplary embodiments, the examples of the subject matter are disclosed below.

EXAMPLES

Materials and Methods
Antibodies

The following antibodies were used: MAB25031 (clone 24-1, R&D systems, USA) and MM13-4 (Upstate,) monoclonal antibodies (mAb) for CFTR detection; Fluorescent secondary antibodies Alexa 594 and 488 were purchased from Molecular Probes (Cergy Pontoise, France)

Cell Culture

Stably transfected HeLa cells (with pTracer plasmid alone as a control (pTracer) or expressing WT-CFTR (spTCF-WT), ΔF508-CFTR s(pTCF-F508del) were provided by Pascale Fanen (Inserm U.468, Créteil, France) and grown as described in Bobadilla J L, Macek M, Jr., Fine J P, Farrell P M. *Cystic fibrosis: a worldwide analysis of CFTR mutations—correlation with incidence data and application to screening*. Hum Mutat, 2002 June; 19(6):575-606. Briefly, HeLa cells were grown in Dulbecco's modified Eagle's medium (DMEM) supplemented with 10% heat-inactivated FCS, 100 U/ml penicillin, 100 μg/ml streptomycin and 250 μg/ml zeocin. Cultures were done at 37° C. in a humidified incubator with 5% $CO_2$. The expression of WT-CFTR and ΔF508-CFTR in these cells was verified by immunoprecipitation and immunocytochemistry throughout the study. Treatments with different molecules (at 1 and 10 μM) and vehicle were done when cells reached 75% confluence.

CF-KM4 cell line, obtained by transformation of primary cultures of CF tracheal gland serous cells homozygous for the ΔF508 mutation by using the wild-type SV40 virus, were grown as described elsewhere in the art (Antigny, F. et al. Calcium homeostasis is abnormal in cystic fibrosis airway epithelial cells but is normalized after rescue of F508del-CFTR. *Cell calcium* 43, 175-83(2008)).

Immunoblot Experiments

Cells cultured in 75 cm$^2$ flasks were washed twice with ice cold PBS, scraped in 2 ml PBS and centrifuged at 600 g for 5 min. The pellets were suspended in 300 μl RIPA buffer (50 mM Tris-HCl, 150 mM NaCl, 1% TritonX-100, 1% Na deoxycholate, 0.1% SDS, pH 7.5) at 4° C. for 30 min with agitation After centrifugation at 15000 g for 30 min the supernatants were processed for immunoblot experiments as previously described in the art (Baudouin-Legros, M. et al. Control of basal CFTR gene expression by bicarbonate-sensitive adenylyl cyclase in human pulmonary cells. *Cellular physiology and biochemistry: international journal of experimental cellular physiology, biochemistry, and pharmacology* 21, 75-86(2008)) with slight modifications.

The samples were resolved by 8% SDS-PAGE, transferred onto PVDF membranes and analysis was performed following manufacturer's recommendations for the Odyssey infrared imaging system (LI-COR Biosciences, NE, USA). Blot membranes were blocked with Odyssey buffer (ScienceTec, Paris, France) for 1 hour and hybridized using monoclonal anti CFTR Mab24-1 (1/1000). The proteins were visualized by incubation with secondary antibodies (1/10000) and detected using ECL technique as described in, Bensalem, N. et al. Down-regulation of the anti-inflammatory protein annexin A1 in cystic fibrosis knock-out mice and patients. *Molecular & cellular proteomics*: MCP 4, 1591-601(2005).

Immunofluorescence Staining

HeLa cells grown on glass coverslips were treated as above and as described in Lipecka, J. et al., Distribution of ClC-2 chloride channel in rat and human epithelial tissues. *American journal of physiology. Cell physiology* 282, C805-16(2002). Cells were fixed with 4% formaldehyde and permeabilized with 0.1% Triton in PBS. Cells were blocked with 1% bovine serum albumine in PBS/Triton and incubated at 4° C. overnight with the primary antibodies, 24-1 (1:300). After washing and blocking with 5% normal goat serum, cells were incubated with the secondary antibodies. Glass coverslips were mounted using the Vectashield mounting medium (Vector laboratories) and examined by confocal laser microscopy (Zeiss, LSM 510).

Iodide Efflux Experiments

CFTR chloride channel activity was assayed by measuring iodide ($^{125}$I) efflux from transfected CHO cells as described previously in the art, Marivingt-Mounir, C, et al., *Synthesis, SAR, crystal structure, and biological evaluation of benzoquinoliziniums as activators of wild-type and mutant cystic fibrosis transmembrane conductance regulator channels*. J Med Chem, 2004. 47(4): p. 962-72. Marivingt-Mounir, C, et al., *Synthesis, SAR, crystal structure, and biological evaluation of benzoquinoliziniums as activators of wild-type and mutant cystic fibrosis transmembrane conductance regulator channels*. J Med Chem, 2004. 47(4): p. 962-72. Cells grown for 4 days in 96-well plates were washed twice with 2 ml of modified Earle's salt solution containing 137 mM NaCl, 5.36 mM KCl, 0.4 mM Na$_2$HPO$_4$, 0.8 mM MgCl$_2$, 1.8 mM CaCl$_2$, 5.5 mM glucose, and 10 mM HEPES, pH 7.4. Cells were then incubated in the same medium containing 1 mM KI (1 mCi of Na$^{125}$I/ml, NEN Life Science Products) for 30 min at 37° C. After washing, cells were incubated with 1 ml of modified Earle's salt solution. After 1 min, the medium was removed to be counted and was quickly replaced by 1 ml of the same medium. This procedure was repeated every 1 min for 8 min. The first three aliquots were used to establish a stable baseline in efflux buffer alone. Medium containing cocktail aiming to increase intracellular cAMP (10 µM forskolin and 30 µM genistein) was used for next aliquots in order to activate CFTR chloride channels. At the end of the incubation, the medium was recovered, and cells were solubilized in 1 N NaOH. The radioactivity was determined using a g-counter (LKB). The total amount of $^{125}$I (in cpm) at time 0 was calculated as the sum of cpm counted in each 1-min sample plus the cpm in the NaOH fraction. The fraction of initial intracellular $^{125}$I lost during each time point was determined, and time-dependent rates of $^{125}$I efflux were calculated according to the art in, Becq, F., et al., *Development of substituted Benzo[c]quinolizinium compounds as novel activators of the cystic fibrosis chloride channel* J Biol Chem, 1999. 274(39): p. 27415-25, from $\ln(^{125}I_{t1}/^{125}I_{t2})/(t_1-t_2)$, where $^{125}$It is the intracellular $^{125}$I at time t; and $t_1$ and $t_2$ are successive time points.

Curves were constructed by plotting rate of $^{125}$I efflux versus time. Data are presented as the mean±S.E. of n separate experiments.

Differences were considered statistically significant using the Student's t test when the p value was less than 0.05.

Whole Cell Patch-Clamp Recordings

Technique for patch-clamp recordings in the whole cell configuration has been described, such as in Hinzpeter, A. et al. *Association between Hsp90 and the ClC-2 chloride channel upregulates channel function*. American journal of physiology. Cell physiology 290, C45-56(2006) and Tanguy, G. et al. *CSN5 binds to misfolded CFTR and promotes its degradation*. Biochimica et biophysica acta 1783, 1189-99 (2008). Stably transfected cells were plated in 35 mm cell culture plastic Petri dishes that were mounted on the stage of an inverted microscope. Patch-clamp experiments were performed at room temperature with an Axopatch 200A amplifier controlled by a computer via a digitdata 1440 interface (Axon Intruments, USA). Pipettes were pulled from hard glass (Kimax 51) using a Setter micropipette puller and their tips were fire-polished. Current recordings were performed using the nystatin-perforated patch clamp configuration. Nystatin stock solution (50 mg/ml) was prepared daily in DMSO. The stock solution was diluted (1:250) in the internal solution which was then sonicated during 1 minute. The internal solution contained the following (in mM): 131 NaCl, 2 MgCl$_2$, and 10 Hepes-Na$^+$, pH 7.3, adjusted with NaOH. The bath solution contained (in mM): 150 NaCl, 1 CaCl$_2$, 1 MgCl$_2$, 35 sucrose and 10 Hepes-Na$^+$, pH 7.3, adjusted with NaOH.

Currents were recorded by application of regular voltage pulses of 60 mV amplitude during 1 second, from a holding potential of 0 mV, with an interval of 3 seconds.

To establish I-V curves, regular voltage pulses were interrupted by series of 9 voltage jumps (1-s duration each), toward membrane potentials between −100 and +80 mV. CFTR Cl-currents were activated with 200 µm 8-(4-chlorophenylthio)-cAMP sodium salt (CPT-cAMP) plus 100 µM 3-isobutyl-1-methylxanthine (IBMX).

When maximal stimulation was reached, cells were bathed with 5 µM of the specific CFTRinhibitor, CFTR$_{inh}$-172, added to the CPT-cAMP solution. CFTR-currents were defined as the differences in current amplitudes recorded during maximum stimulation by CPT-cAMP and after inhibition by CFTR$_{inh}$-172.

Nasal Potential Difference (NPD) Measurements

The method for nasal potential measurement was adapted and miniaturised from the technique developed for young children as shown in Sermet-Gaudelus, I. et al. *Measurement of nasal potential difference in young children with an equivocal sweat test following newborn screening for cystic fibrosis*. Thorax 65, 539-44(2010). Mice were anesthetized by an intraperitoneal injection of ketamine (133 mg/kg; IMALGENE 1000, MERIAL, France) and xylazine (13.3 mg/kg; Rompun 2%, BayerPharma, France). Mice were positioned on a 45° tilt board and a paper pad was placed under the nose to avoid mice quelling. A subcutaneous needle was connected to an Ag$^+$/AgCl reference electrode by an agar bridge. A double-lumen polyethylene catheter (0.5 mm diameter) was inserted into one nostril 4 mm depth. One lumen perfused by a Ringer solution (in mM: 140 NaCl, 6 KCl, 10 Hepes, 10 Glucose, 1 MgCl2, 2 CaCl2, pH adjusted to 7,4 with NaOH) at 0.15 mL/h is connected to a measuring Ag$^+$/AgCl electrode. The two Ag$^+$/AgCl electrodes were connected to a high-impedance voltmeter (LOGAN research Ltd, United Kingdom). The second lumen perfused solution with the following sequence: (1) Ringer solution, (2) Ringer solution containing amiloride (inhibitor of Na$^+$ conductance, 100 µM), (3) Low Chloride Ringer solution, to unmask Cl$^-$ conductances (in mM: 140 Na gluconate, 6 K gluconate, 10 Hepes, 10 Glucose, 1 MgCl$_2$, 6 Ca-gluconate, pH adjusted to 7.4 with NaOH), (4) Low Chloride Ringer solution containing CFTR inhibitor-172 (5 µM, Calbiochem, Germany) to evaluate the participation of CFTR. Each solution was perfused at least 3 minutes, and 30 seconds stability was required before perfusion switch. Steady state transepithelial potential, $V_{TE}$, $\Delta V_{TEAmil}$ (difference between $V_{TE}$ and transepithelial potential recorded after perfusion of amiloride-containing solution), $\Delta V_{TEamilLowCl}$ (difference between $V_{TE}$ and transepithelial potential recorded after perfusion with Low Cl$^-$ plus amiloride-containing solution) and $\Delta V_{TEamilLowClInh-172}$ (difference between $V_{TE}$ and after addition of CFTR inhibitor to the previous solution) were the means of 30 values recorded during stability.

MTT Cell Viability Assay

To determine cell viability the typical MTT assay was used. HeLa cells were cultured in a 96-well plate and exposed to varying concentrations of compounds disclosed herein for 24 h. After washing, MTT solution and medium were then introduced. After incubation, the resultant formazan crystals were dissolved in dimethyl sulfoxide and the absorbance intensity measured by a microplate reader at 570 nm.

Virtual Screening—Identification of Modulator Compounds

A database of a low molecular weight compounds was used in the virtual screening process as a source of hits. Molecular docking program Dock 6.1 was used to test a conformational space of small molecules inside two potential binding sites on the protein surface. Subsequently, all selected ligands and whole complexes were fully minimized in force field. At each step, a set of scoring functions was used for rating of potential complexes and appropriate molecules were selected for experimental tests.

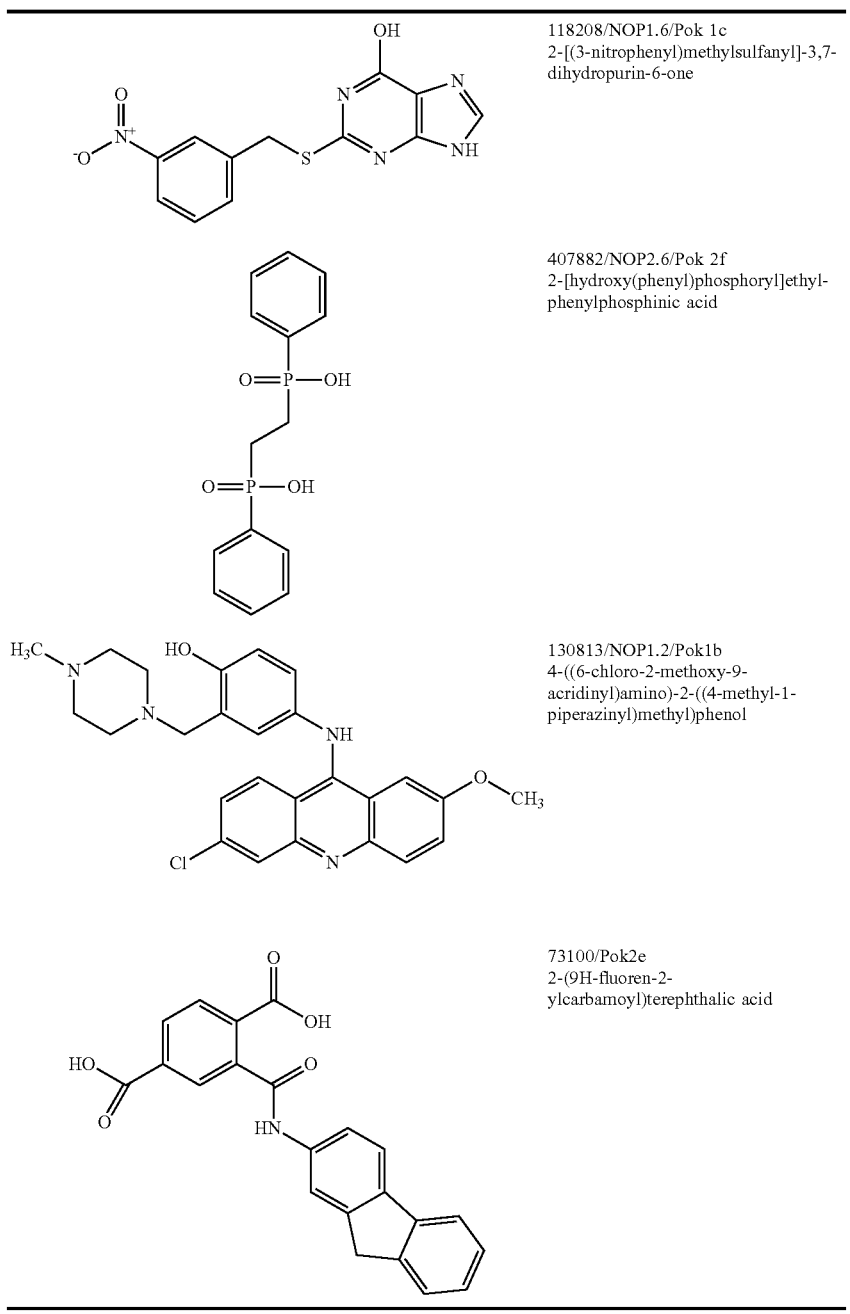

118208/NOP1.6/Pok 1c
2-[(3-nitrophenyl)methylsulfanyl]-3,7-dihydropurin-6-one

407882/NOP2.6/Pok 2f
2-[hydroxy(phenyl)phosphoryl]ethyl-phenylphosphinic acid

130813/NOP1.2/Pok1b
4-((6-chloro-2-methoxy-9-acridinyl)amino)-2-((4-methyl-1-piperazinyl)methyl)phenol 73100/Pok2e
2-(9H-fluoren-2-ylcarbamoyl)terephthalic acid Yellow MTT is reduced to purple formazan in living cells. The absorbance of this colored solution can be quantified by measuring at a certain wavelength by a spectrophotometer. This conversion can be directly related to the number of viable (living) cells.

Results

Effect of Drugs on Iodide, I—, Efflux

To test drug correction of ΔF508-CFTR trafficking and function we evaluated halide permeability by a macroscopic assay using a robotic cell-based methodology using the I$^-$ efflux technique. In the first series of experiments, the potential corrector effects were tested by 24 hour pretreatment of ΔF508-CFTR HeLa cells with all compounds at 1 μM followed by measurements of cAMP-dependent radiolabel iodide efflux. Treatments with compounds 130813 and 118208 on pocket 1 and 73100 and 407882 on pocket 2, lead to significant increase of cAMP-stimulated radiolabel iodide efflux (FIG. 1a), the most potent being 407882. At this low dose (1 μM) the increase in the cAMP-stimulated efflux was lower than that observed using 100 μM of the known corrector miglustat(27). Examples of I⁻ efflux stimulation after treatment with each of the four active compounds are illustrated in FIG. 1b. cAMP-stimulated I⁻ efflux was completely prevented when experiments were performed in the presence of the CFTR channel blocker $CFTR_{inh}$-172.

Figure 2:
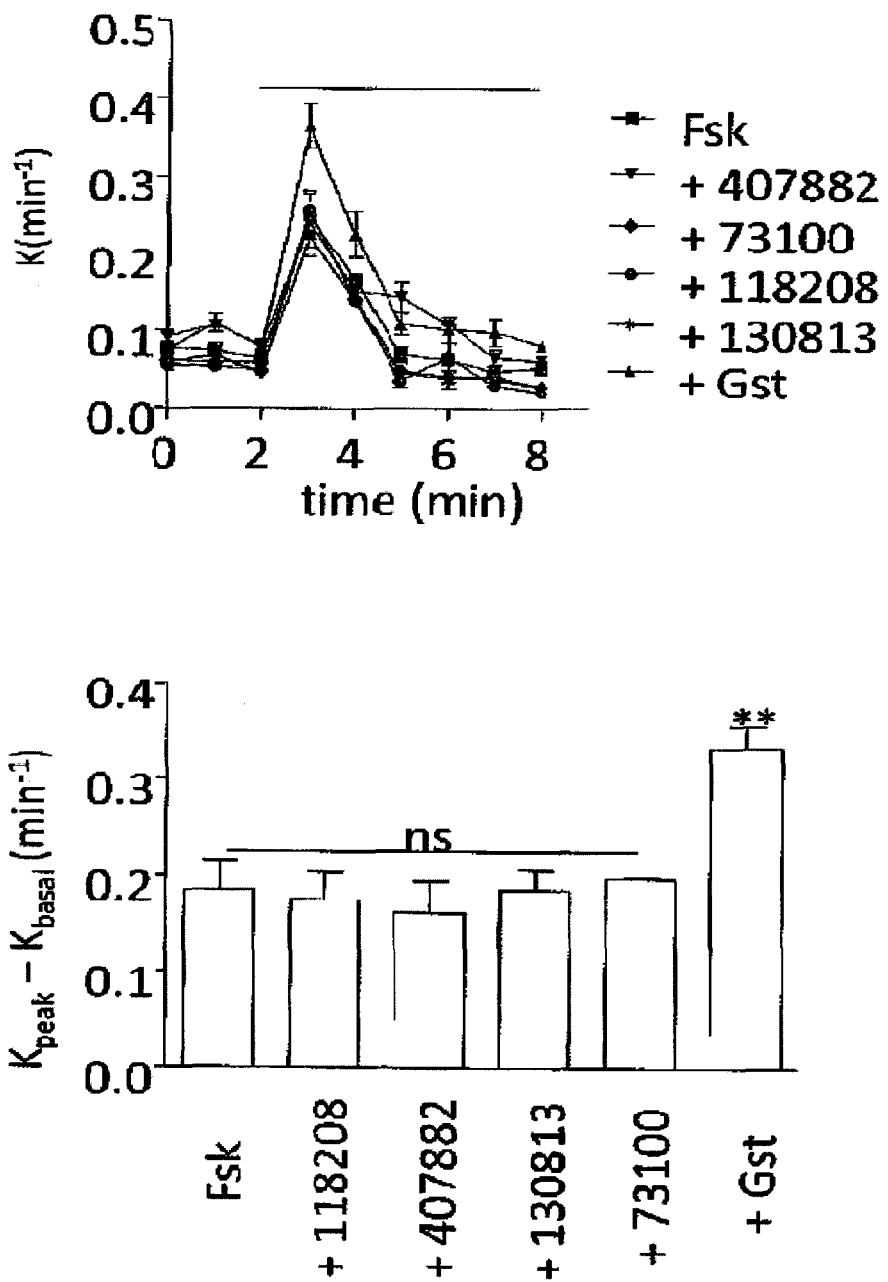
FIG. 2 indicates iodide efflux in untreated WT-CFTR HeLa cells.

We further tested the effect of the four compounds in a wide range of concentrations and determined $EC_{50}$ for pocket 1 compound 130813, and two pocket 2 compounds 407882 and 73100 at 1 μM, 10 μM and 844 nM, respectively (FIG. 1c). The $EC_{50}$ for pocket 1—118208 could not be precisely determined since the maximum iodide efflux was not reached even at 100 μM (FIG. 1d). Notably, the effect of compound 407882 could be increased by 3-fold when used at 10 μM, reaching a stimulated efflux comparable to the value observed for WT-CFTR (FIG. 2).

Figure 3:
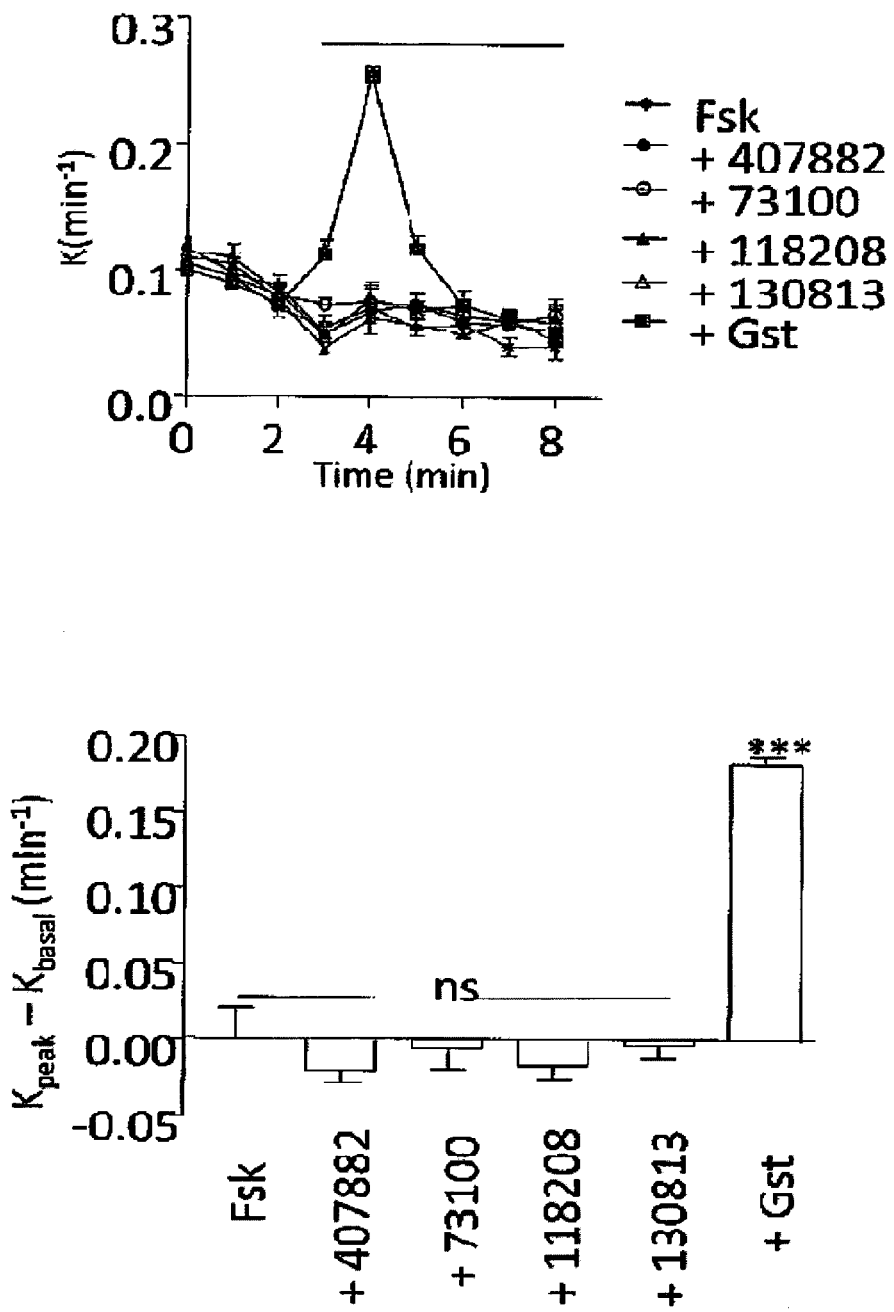
FIG. 3 indicates iodine efflux in ΔF508-CFTR HeLa cells with forskolin alone, forskolin plus genistein or forskolin plus other compounds.

To test whether the compounds exhibit potentiator activity independent of their effect on CFTR trafficking, we examined iodide efflux in untreated WT-CFTR HeLa cells. Compounds were added along with forskolin and their effects were compared to that of forskolin alone or forskolin plus genistein. Unlike genistein, all tested molecules induced an I⁻ efflux greater than that of forskolin alone (FIG. 2). Potentiation was also tested in ΔF508-CFTR HeLa cells treated for 2 hours with miglustat to rescue ΔF508-CFTR. I⁻ efflux was stimulated either with forskolin alone, with forskolin plus genistein or forskolin plus the different compounds. As shown in FIG. 3, only genistein was able to increase efflux, demonstrating the absence of potentiation activity by our drugs.

Effect of Drugs on CFTR Maturation

Figure 4:
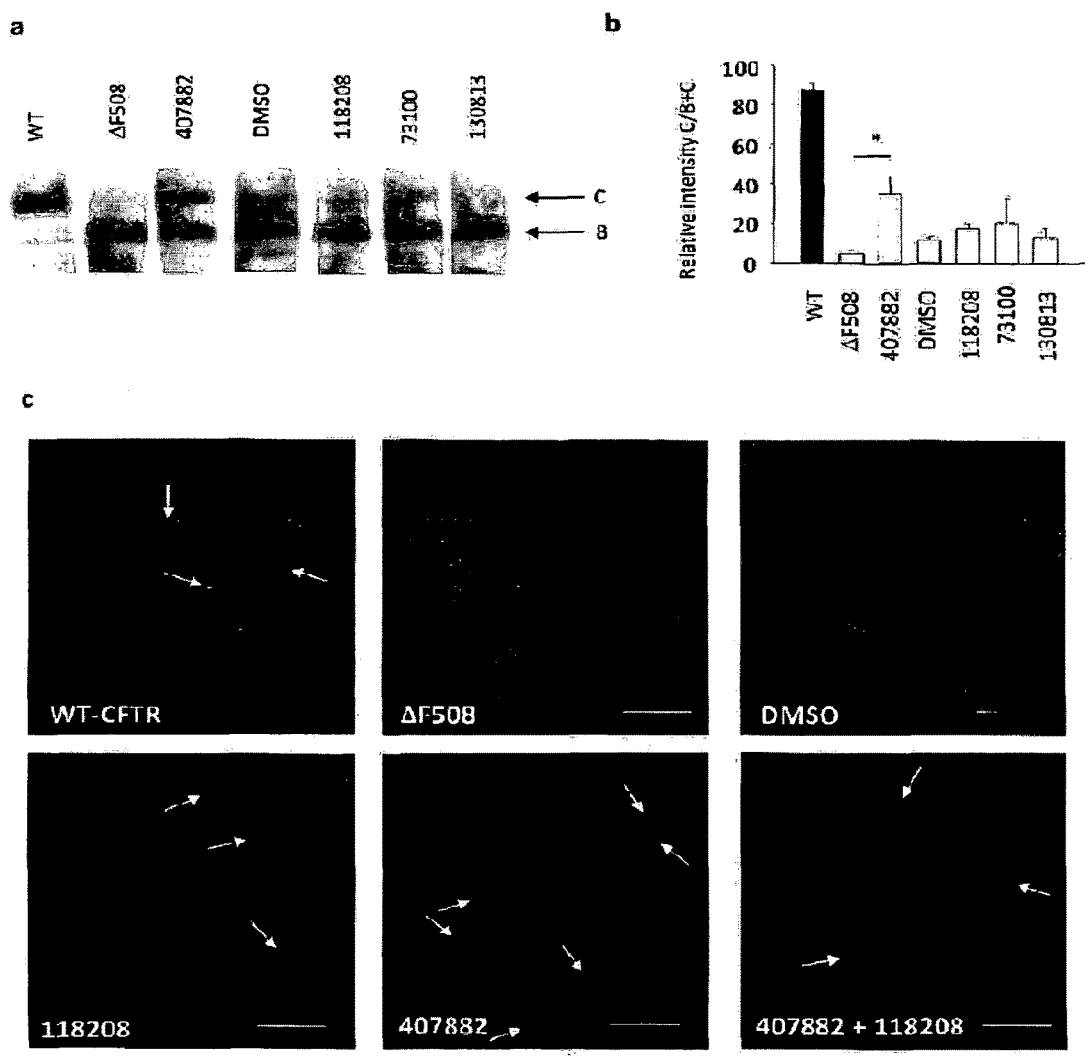
FIG. 4 indicates the impact of correctors on ΔF508-CFTR maturation and cell localization.

The efficacy of the four compounds as correctors for ΔF508-CFTR trafficking was further validated by immunoblotting. We assumed that detection of a fully glycosylated band C suggests correct processing of ΔF508-CFTR. A representative immunoblot is shown in FIG. 4a. Anti-CFTR antibodies detect two bands in proteins derived from WT-CFTR cells, (line WT-CFTR in FIG. 4a). The diffuse band of approximately 170 kDa (band C) corresponds to a mature, fully glycosylated protein that has processed through the Golgi apparatus. The band below of about 145 kDa corresponds to the immature core-glycosylated protein located in the endoplasmic reticulum. In ΔF508-CFTR expressing cells, only the immature protein is detectable (line ΔF508 in FIG. 4a). Band C was clearly detectable in cells treated with 1 μM of compound 407882 as compared to untreated cells, whereas the signal at 170 kDa was not different from DMSO treatment in cells treated with 1 μM of compounds 118208, or 130813 or very slightly increased in cells treated by 1 μM of compound 73100. None of the compounds modified total protein expression. The relative abundance of mature CFTR, expressed as the ratio of band C to band C+band B is shown in FIG. 4b. Only compound 407882 increased significantly the relative abundance of mature CFTR.

Effect of Drugs on CFTR Immunolocalization

FIG. 4c shows typical CFTR staining at the plasma membrane in WT-CFTR expressing HeLa cells whereas ΔF508-CFTR was found throughout the cytoplasm. Treatment of cells for 24 hours with 1 μM of 407882 resulted in a clear CFTR staining at or near the plasma membrane, indicating rescue of ΔF508-CFTR trafficking in agreement with immunoblot experiments. When cells were treated by each of the three other compounds, 118208, 73100 or 130813, a discrete punctuate staining at the plasma membrane was observed in a small fraction of cells, as illustrated for compound 118208 in FIG. 4c.

Combined Effect of Compounds Binding to Different Pockets.

Figure 5:
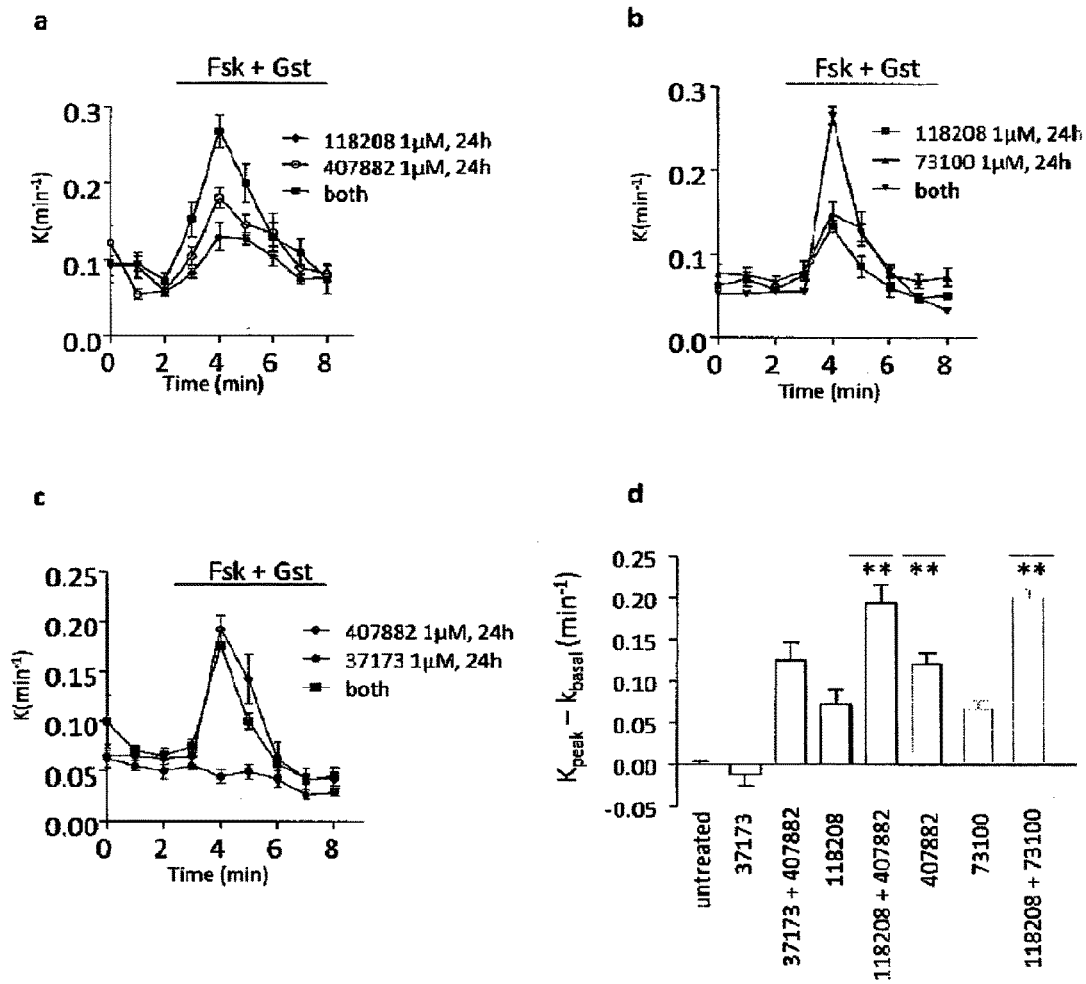
FIG. 5 indicates synergistic effects of active compounds on iodide efflux.

If two compounds are able to correct ΔF508-CFTR by binding to the same protein conformation but at different surface cavities their effects could be additive or synergistic. We tested this hypothesis by two independent types of assays, namely iodide efflux and patch clamp. The results from iodide permeability tests (FIG. 5) showed that combined treatment of cells with compounds 118208 plus 407882 (FIG. 5a) or with 118208 plus 73100 (FIG. 5b) at 1 μM of each, leads to greater cAMP-dependent anion fluxes than those observed with any of the molecules alone. In this series of experiments the compound 37173 (FIG. 5c) was used as a control as it did not induce any cAMP-stimulated iodide efflux at the same concentration. As shown in FIG. 5c, co-treatment of ΔF508-CFTR HeLa cells with 37173 plus 407882 induced cAMP-stimulated iodide efflux with an amplitude similar to 407882 treatment alone. By contrast, co-treatment with compounds 118208 and 407882 induced iodide efflux with an amplitude equal to the sum of effluxes induced by each compound, whereas a slight synergistic effect was observed after treatment by 118208 plus 73100.

Figure 6:
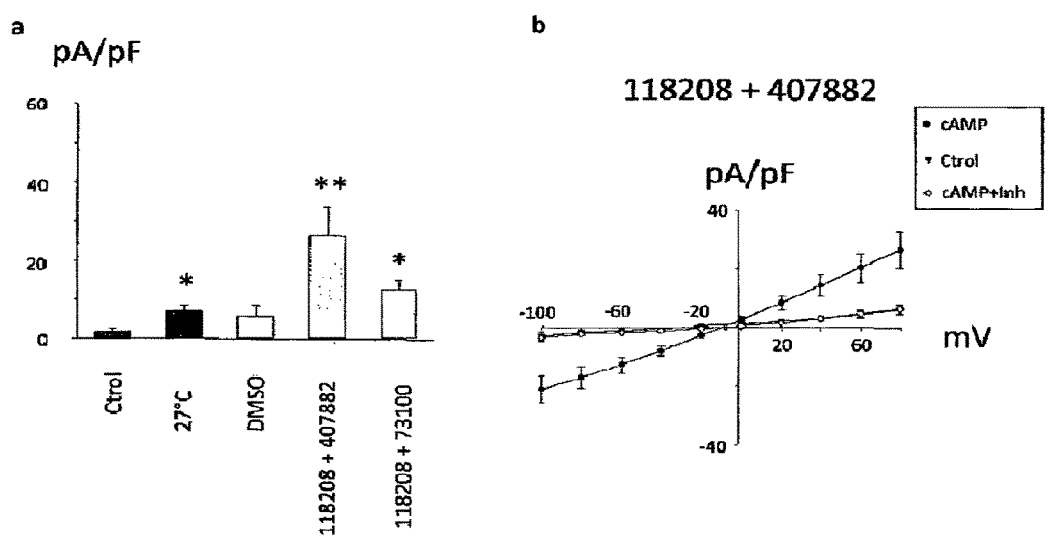
FIG. 6 indicates current-voltage relationship for cAMP-dependent chloride currents in HeLa cells.

The activity of the different compounds was also evaluated in patch-clamp experiments. FIG. 6a summarizes the mean values of current amplitudes recorded at −60 mV in the different experimental conditions. CFTR-related current density ($I_{\Delta F508\text{-}CFTR}$; pA/pF) is defined as cAMP-stimulated current minus the current recorded after inhibition by CFTR inh-172 at 5 μM, and normalized to cell capacitance. $I_{\Delta F508\text{-}CFTR}$ was very low in untreated cells and stimulated by around 3-fold when cells were cultured at 27° C. for 24 hours before recordings. Treatment of cells for 24 h with 1 μM of either 118208, 407882 or 73100 alone, did not increase current amplitude as compared to their respective controls (data not shown). However, 24 h pre-treatment with 1 μM of 118208 plus 407882 or 118208 plus 73100 showed a significant increase in $I_{\Delta F508\text{-}CFTR}$. Examples of linear I/V plots from cells pretreated by 118208 plus 407882 before stimulation, in the presence of cptcAMP+IBMX and after inhibition by CFTRinh-172 are shown in FIG. 6b.

Effects of 407882 and 118208 on CF-4KM Cells

Figure 7:
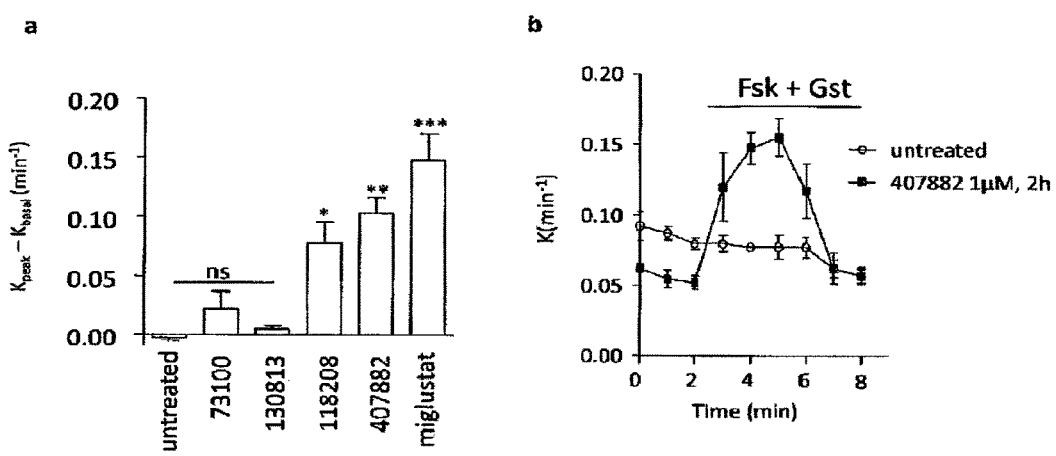
FIG. 7 indicates effects of different compounds on iodide efflux.
Figure 8:
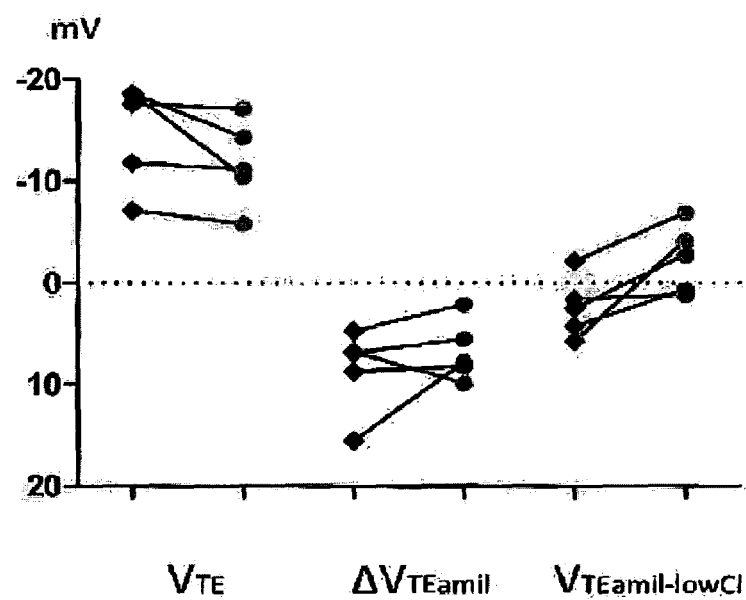
FIG. 8 indicates the effect of 73100 plus 118208 molecules on nasal potential difference (6VTE) in 6F508/M508 mice.

The effects of the four molecules active in HeLa cells were next tested on CFTR-dependent iodide efflux in an epithelial serous cell line derived from a ΔF508 CF patient (CF-KM4) expressing low amounts of endogenous ΔF508-CFTR. In these epithelial cells compounds 407882 and 118208 were still able to induce significant cAMP-dependent iodide efflux (FIG. 7). However, it must be noted that 2 molecules correcting ΔF508-CFTR in Hela cells (130813 and 73100) were not active in this cell line.

Effects of 73100 Plus 118208 on Nasal Potential Difference in ΔF508 Mice.

Our results in cells suggested that the pairs of molecules acting on different pockets display additive correcting effects. To test if these molecules are active in vivo, nasal potential difference ($\Delta V_{TE}$) was monitored (as in Sermet-Gaudelus, I. et al., *Measurement of nasal potential difference in young children with an equivocal sweat test following newborn screening for cystic fibrosis*. Thorax 65, 539-44 (2010)) in ΔF508/ΔF508 mice treated intranasally for 24 hours with 30 μl of 73100 plus 118208 molecules (0.1 μmol each) embedded in liposomes (5:1) or with liposomes alone. In ΔF508 mice, basal $V_{TE}$ values and $\Delta V_{TE}$ changes induced by perfusion of nasal epithelium with 100 μM amiloride, $\Delta V_{TEamil}$ were similar in mice treated with the two molecules or with liposomes alone. By contrast, perfusion of low Cl⁻ solution in 3 out of 5 mice hyperpolarized $V_{TE}$ by more than 2 mV ($\Delta V_{TEamil-lowCl}$) i.e. the threshold value established by us as significant effect of treatment (manuscript in preparation). The CFTR-related current unmasked by CFTR inhibitor $I_{Inh172}$ represents about 30% of ($\Delta V_{TEamil-lowCl}$) (data not shown).

The following references are incorporated herein in their entirety:

1. Ollero M, Brouillard F, Edelman A. Cystic fibrosis enters the proteomics scene: new answers to old questions. Proteomics, 2006 July; 6(14):4084-99.
2. Riordan J R, Rommens J M, Kerem B, Alon N, Rozmahel R, Grzelczak Z, et al. Identification of the cystic fibrosis gene: cloning and characterization of complementary DNA. Science, 1989 Sep. 8; 245(4922):1066-73.
3. Rommens J M, Iannuzzi M C, Kerem B, Drumm M L, Melmer G, Dean M, et al. Identification of the cystic fibrosis gene: chromosome walking and jumping. Science, 1989 Sep. 8; 245(4922): 1059-65.
4. Castellani C, Cuppens H, Macek M, Jr., Cassiman J J, Kerem E, Durie P, et al. Consensus on the use and interpretation of cystic fibrosis mutation analysis in clinical practice. J Cyst Fibros, 2008 May; 7(3): 179-96.
5. Cystic Fibrosis Mutation Database http://www.genet.sickkids.on.ca/cftr/app.
6. Welsh M J, Smith A E. Molecular mechanisms of CFTR chloride channel dysfunction in cystic fibrosis. Celi, 1993 Jul. 2; 73(7): 1251-4.
7. Wilschanski M, Zielenski J, Markiewicz D, Tsui L C, Corey M, Levison H, et al. Correlation of sweat chloride concentration with classes of the cystic fibrosis transmembrane conductance regulator gene mutations. J Pediatr, 1995 November; 127(5):705-10.
8. Ward C L, Omura S, Kopito R R. Degradation of CFTR by the ubiquitin-proteasome pathway. Cell, 1995 Oct. 6; 83(1):121-7.
9. Bobadilla J L, Macek M, Jr., Fine J P, Farrell P M. Cystic fibrosis: a worldwide analysis of CFTR mutationscorrelation with incidence data and application to screening. Hum Mutat, 2002 June; 19(6):575-606.
10. Lewis H A, Zhao X, Wang C, Sauder J M, Rooney I, Noland B W, et al Impact of the deltaΔF508 mutation in first nucleotide-binding domain of human cystic fibrosis transmembrane conductance regulator on domain folding and structure. J Biol Chem, 2005 Jan. 14; 280(2): 1346-53.
11. Schwiebert E M, Benos D J, Egan M E, Stutts M J, Guggino W B. CFTR is a conductance regulator as well as a chloride channel. Physiol Rev, 1999 January; 79(1 Suppl):S145-66.
12. Reddy M M, Light M J, Cjuinton P M. Activation of the epithelial Na+ channel (ENaC) requires CFTR Cl− channel function. Nature, 1999 Nov. 18; 402(6759):301-4.
13. Ahmed N, Corey M, Forstner G, Zielenski J, Tsui L C, Ellis L, et al. Molecular consequences of cystic fibrosis transmembrane regulator (CFTR) gene mutations in the exocrine pancreas. Gut, 2003 August; 52(8): 1159-64.
14. Riordan J R. Assembly of functional CFTR chloride channels. Annu Rev Physiol, 2005; 67:701-18.
15. Allen M P, Tildesley D J. Computer simulation of liquids: Oxford, Clarendon Press; 1987.
16. Jungas, T., et al., *Glutathione levels and BAX activation during apoptosis due to oxidative stress in cells expressing wild-type and mutant cystic fibrosis transmembrane conductance regulator.* J Biol Chem, 2002. 277(31): p. 27912-8.
17. Antigny, F. et al. Calcium homeostasis is abnormal in cystic fibrosis airway epithelial cells but is normalized after rescue of F508del-CFTR. *Cell calcium* 43, 175-83 (2008).
18. Baudouin-Legros, M. et al. Control of basal CFTR gene expression by bicarbonate-sensitive adenylyl cyclase in human pulmonary cells. *Cellular physiology and biochemistry: international journal of experimental cellular physiology, biochemistry, and pharmacology* 21, 75-86 (2008).
19. Bensalem, N. et al. Down-regulation of the anti-inflammatory protein annexin A1 in cystic fibrosis knock-out mice and patients. *Molecular & cellular proteomics: MCP* 4, 1591-601(2005).
20. Lipecka, J. et al. Distribution of ClC-2 chloride channel in rat and human epithelial tissues. *American journal of physiology. Cell physiology* 282, C805-16(2002).
21. Marivingt-Mounir, C, et al., *Synthesis, SAR, crystal structure, and biological evaluation of benzoquinoliziniums as activators of wild-type and mutant cystic fibrosis transmembrane conductance regulator channels.* J Med Chem, 2004. 47(4): p. 962-72.
22. Becq, F., et al., *Development of substituted Benzo[c]quinolizinium compounds as novel activators of the cystic fibrosis chloride channel.* J Biol Chem, 1999. 274(39): p. 27415-25.
23. Hinzpeter, A. et al. Association between Hsp90 and the ClC-2 chloride channel upregulates channel function. *American journal of physiology. Cell physiology* 290, C45-56(2006).
24. Tanguy, G. et al. CSN5 binds to misfolded CFTR and promotes its degradation. *Biochimica et biophysica acta* 1783, 1189-99(2008).
25. Sermet-Gaudelus, I. et al. Measurement of nasal potential difference in young children with an equivocal sweat test following newborn screening for cystic fibrosis. *Thorax* 65, 539-44(2010).
26. Norez, C. et al. Maintaining low Ca2+ level in the endoplasmic reticulum restores abnormal endogenous F508del-CFTR trafficking in airway epithelial cells. *Traffic (Copenhagen, Denmark)* 7, 562-73(2006).
27. Norez, C. et al. Rescue of functional delF508-CFTR channels in cystic fibrosis epithelial cells by the alpha-glucosidase inhibitor miglustat. *FEBS letters* 580, 2081-6(2006).

Of course these methods are exemplary and alterations thereto are possible by those having skill in the relevant technology.

Thus the example embodiments and arrangements achieve improved capabilities, eliminate difficulties encountered in the use of prior methods and systems, and attain the desirable results described herein.

In the foregoing description, certain terms have been used for brevity, clarity and understanding. However, no unnecessary limitations are to be implied therefrom because such terms are used for descriptive purposes and are intended to be broadly construed.

Moreover the descriptions and illustrations herein are by way of examples and the inventive scope is not limited to the features shown and described.

Further, it should be understood that features and/or relationships associated with one embodiment can be combined with features and/or relationships from other embodiments. That is, various features and/or relationships from various embodiments can be combined in further embodiments. The inventive scope of the disclosure is not limited to only the embodiments shown or described herein.

Having described the features, discoveries and principles of the exemplary embodiments, the manner in which they are utilized and carried out, and the advantages and useful results attained, the new and useful arrangements, combinations, methodologies, structures, devices, elements, combinations, operations, processes and relationships are set forth in the appended claims.

We claim:
1. A pharmaceutical composition comprising:
a compound of general formula (IIIb) used for the manufacture of a medication for the treatment of diseases associated with CFTR protein malfunction:

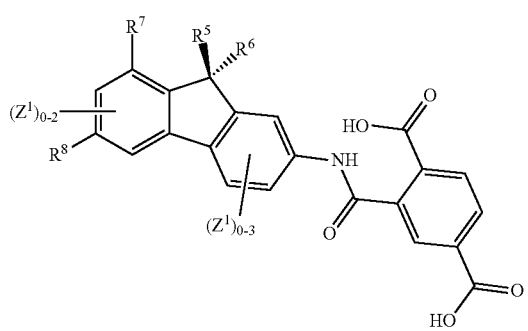

(IIIb)

its tautomers, E and Z geometric isomers, enantiomers, diastereomers, or pharmaceutically acceptable salts thereof or complexes thereof;
wherein any occurrence of $Z^1$ independently represents the following optional substituents, —$OR_B$, —OC(=O)$R_C$, —OC(=O)$OR_B$, —OC(=O)N($R_A$)$R_A$', —C(=O)$R_C$, —C(=O)N($R_A$)$R_A$', —C(=O)N($OR_B$)$R_A$, —C(=O)$OR_B$, —C(=S)$R_C$, —C(=O)C(=O)$R_C$, —$CH_2OR_B$, —$CH_2CH_2OR_B$, —$CH_2N(R_A)R_A$', —$CH_2CH_2N(R_A)R_A$', —$CH_2OCH_2R_C$, —$CH_2N(R_A)CH_2R_C$, —$SR_D$, —S(=O)$R_D$, —$SO_2R_D$, —$SO_2N(R_A)R_A$', —$SO_3R_B$, —N($R_A$)C(=O)$R_C$, —N($R_A$)C(=O)$OR_B$, —N($R_A$)C(=O)N($R_A$')$R_A$'', —N($R_A$)$SO_2R_D$, —N($R_A$)$SO_2$N($R_A$')$R_A$'', —N($R_A$)$R_A$', —N($R_A$)C(=O)$R_C$, —N($R_A$)C(=O)$OR_B$, —N($R_A$)N($R_A$')$R_A$'', —N($R_A$')N($R_A$)C(=O)$R_C$, —$NO_2$, —CN, —$CF_3$, —$CHF_2$, —$CH_2F$, —$NH_2$, —SCN, —$SO_2CN$, —F, Cl, —Br, —I, —$C_nH_{2n}R_C$ which is branched or unbranched wherein n is an integer from 1 to 5; —$C_nH_{(2n-2)}R_C$ in E or Z geometrical conformation which is branched or unbranched wherein n is an integer from 2 to 5; —$C_nH_{(2n-4)}R_C$ which is branched or unbranched wherein n is an integer from 2 to 5, —$PO_3H_2$, or —$OPO_3H_2$;

wherein $R_A$, $R_A$', $R_A$" are each independently selected from the group consisting of: —H, lower alkyl group, —CN, —$CF_3$, —$CHF_2$, —$CH_2F$, and —OH;
wherein $R_B$ is independently selected from the group consisting of: —H, lower alkyl group, —CN, —$CF_3$, —$CHF_2$, —$CH_2F$, —$CH_2Cl$, —$CH_2Br$, and —$CH_2I$;
wherein $R_C$ is independently selected from the group consisting of: —H, lower alkyl group, —CN, —$CF_3$, —$CHF_2$, —$CH_2Cl$, —$CH_2Br$, —$CH_2I$, —F, —Cl, —Br, —I, and —$NH_2$;
wherein $R_D$ is independently selected from the group consisting of: —H and lower alkyl group
wherein $R^5$ and $R^6$ are optional substituents which are independently selected from the group consisting of: OH, $NH_2$, COOH, Cl, Br, I, $CH_3$, and $C_2H_5$;
wherein $R^7$ is an optional substituent which is independently selected from the group consisting of: —F, —Cl, —Br, —I, —$CH_3$, and —$C_2H_5$;
wherein $R^8$ is an optional substituent which is independently selected from the group consisting of: —$NH_2$, —NHAr, —OH, —$CH_2Ar$, —C(=O)Ar, and —OAr;
wherein Ar is an aromatic group or heteroaromatic group, and
wherein the compound of formula (IIIb) is present in a pharmaceutical composition.

2. The pharmaceutical composition according to claim 1, wherein the compound has an effect on mutant CFTR protein, wherein said CFTR mutation is a mutation ΔF508-CFTR, or another mutation of class II, and wherein a mutation ΔF508-CFTR, or another mutation of class II are involved in CFTR protein malfunction.

3. The pharmaceutical composition according to claim 1, wherein the compound is characterized in that it has effect on CFTR-dependent ion transport across a cellular membrane and/or it has the ability to increase the number of mutant CFTR proteins that reach a cell surface.

4. The pharmaceutical composition according to claim 1, wherein the compound is characterized in that it has a stabilizing effect on the structure of the mutant CFTR protein and/or blocks interaction with cellular proteins responsible for the premature degradation of mutant CFTR.

5. The pharmaceutical composition according to claim 1, wherein the compound is characterized in that it has an effect on mutant CFTR protein, wherein said CFTR mutation is a mutation ΔF508-CFTR, or another mutation of class II.

6. A pharmaceutical composition comprising:
a compound used for the manufacture of a medication for the treatment of diseases associated with CFTR protein malfunction:

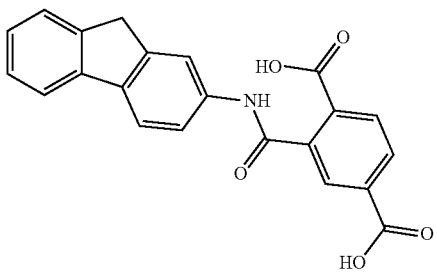 [SMILES: O=C(O)c1ccc(C(=O)O)c(C(=O)Nc2ccc3c(c2)Cc2ccccc2-3)c1]

its tautomers, E and Z geometric isomers, enantiomers, diastereomers or its pharmaceutically acceptable salts thereof, or complexes thereof,
wherein the compound is present in a pharmaceutical composition.

7. The pharmaceutical composition according to claim 6, wherein the compound has an effect on mutant CFTR protein, wherein said CFTR mutation is a mutation ΔF508-CFTR or another mutation of class II, and wherein the mutation ΔF508-CFTR or another mutation of class II are involved in CFTR protein malfunction.

8. The pharmaceutical composition according to claim 6, wherein the compound is characterized in that it has effect on CFTR-dependent ion transport across a cellular membrane and/or it has the ability to increase mutant CFTR proteins that reach a cell surface.

9. The pharmaceutical composition according to claim 6, wherein the compound is characterized in that it has a stabilizing effect on the structure of the mutant CFTR protein and/or blocks interaction with cellular proteins responsible for premature degradation of mutant CFTR protein.

10. The pharmaceutical composition according to claim 6, wherein the compound is characterized in that it has an effect on mutant CFTR protein, wherein said CFTR mutation is a mutation ΔF508-CFTR, or another mutation of class II.

11. A method comprising:
treating a disease associated with CFTR protein malfunction in a patient by administering a therapeutically effective amount of a composition comprising:
a compound:

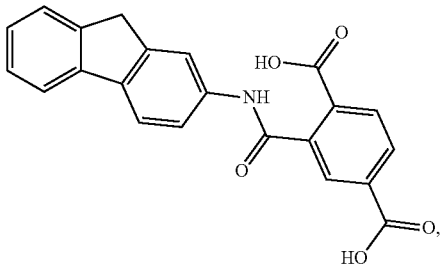 [SMILES: O=C(O)c1ccc(C(=O)O)c(C(=O)Nc2ccc3c(c2)Cc2ccccc2-3)c1]

its tautomers, E and Z geometric isomers, enantiomers, diastereomers or its pharmaceutically acceptable salts thereof, or complexes thereof,
as a modulator of a mutant CFTR protein to the patient.

12. The method according to claim 11, wherein the CTFR protein malfunction is a mutation of ΔF508-CFTR.

13. A method comprising:
treating a disease associated with CFTR protein malfunction in a patient by administering to the patient a therapeutically effective amount of a composition comprising:

a compound of general formula (IIIb):

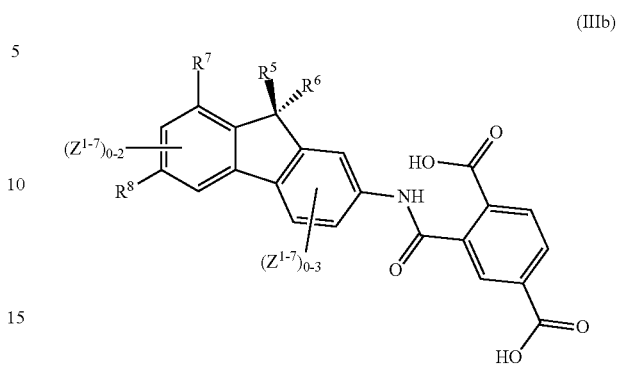

(IIIb)

its tautomers, E and Z geometric isomers, enantiomers, diastereomers, or pharmaceutically acceptable salts thereof or complexes thereof;
wherein any occurrence of $Z^1$ independently represents the following optional substituents, $-OR_B$, $-OC(=O)R_C$, $-OC(=O)OR_B$, $-OC(=O)N(R_A)R_A'$, $-C(=O)R_C$, $-C(=O)N(R_A)R_A'$, $-C(=O)N(OR_B)R_A$, $-C(=O)OR_B$, $-C(=S)R_C$, $-C(=O)C(=O)R_C$, $-CH_2OR_B$, $-CH_2CH_2OR_B$, $-CH_2N(R_A)R_A'$, $-CH_2CH_2N(R_A)R_A'$, $-CH_2OCH_2R_C$, $-CH_2N(R_A)CH_2R_C$, $-SR_D$, $-S(=O)R_D$, $-SO_2R_D$, $-SO_2N(R_A)R_A'$, $-SO_3R_B$, $-N(R_A)C(=O)R_C$, $-N(R_A)C(=O)OR_B$, $-N(R_A)C(=O)N(R_A')R_A''$, $-N(R_A)SO_2R_D$, $-N(R_A)SO_2N(R_A')R_A''$, $-N(R_A)R_A'$, $-N(R_A)C(=O)R_C$, $-N(R_A)C(=O)OR_B$, $-N(R_A)N(R_A')R_A''$, $-N(R_A')N(R_A)C(=O)R_C$, $-NO_2$, $-CN$, $-CF_3$, $-CHF_2$, $-CH_2F$, $-NH_2$, $-SCN$, $-SO_2CN$, $-F$, Cl, $-Br$, $-I$, $-C_nH_{2n}R_C$ which is branched or unbranched wherein n is an integer from 1 to 5; $-C_nH_{(2n-2)}R_C$ in E or Z geometrical conformation which is branched or unbranched wherein n is an integer from 2 to 5; $-C_nH_{(2n-4)}R_C$ which is branched or unbranched wherein n is an integer from 2 to 5, $-PO_3H_2$, or $-OPO_3H_2$;
wherein $R_A$, $R_A'$, $R_A''$ are each independently selected from the group consisting of: $-H$, lower alkyl group, $-CN$, $-CF_3$, $-CHF_2$, $-CH_2F$, and $-OH$;
wherein $R_B$ is independently selected from the group consisting of: $-H$, lower alkyl group, $-CN$, $-CF_3$, $-CHF_2$, $-CH_2F$, $-CH_2Cl$, $-CH_2Br$, and $-CH_2I$;
wherein $R_C$ is independently selected from the group consisting of: $-H$, lower alkyl group, $-CN$, $-CF_3$, $-CHF_2$, $-CH_2Cl$, $-CH_2Br$, $-CH_2I$, $-F$, $-Cl$, $-Br$, $-I$, and $-NH_2$;
wherein $R_D$ is independently selected from the group consisting of: $-H$ and lower alkyl group
wherein $R^5$ and $R^6$ are optional substituents which are independently selected from the group consisting of: OH, $NH_2$, COOH, Cl, Br, I, $CH_3$, and $C_2H_5$;
wherein $R^7$ is an optional substituent which is independently selected from the group consisting of: $-F$, $-Cl$, $-Br$, $-I$, $-CH_3$, and $-C_2H_5$;
wherein $R^8$ is an optional substituent which is independently selected from the group consisting of: $-NH_2$, $-NHAr$, $-OH$, $-CH_2Ar$, $-C(=O)Ar$, and $-OAr$;
wherein Ar is an aromatic group or heteroaromatic group.

14. The method according to claim 13, wherein the CTFR protein malfunction is a mutation of ΔF508-CFTR.

* * * * *